US010576106B2

(12) United States Patent
Han

(10) Patent No.: US 10,576,106 B2
(45) Date of Patent: Mar. 3, 2020

(54) MUSCULOSKELETAL STEM CELL AND MEDIUM FOR INDUCING DIFFERENTIATION OF MUSCULOSKELETAL STEM CELL

(71) Applicant: CELLATOZ THERAPEUTICS, INC., Seongnam-si, Gyeonggi-do (KR)

(72) Inventor: Myung-Kwan Han, Jeonju-si (KR)

(73) Assignee: Cellatoz Therapeutics, Inc., Gyeonggi (KR)

(*) Notice: Subject to any disclaimer, the term of this patent is extended or adjusted under 35 U.S.C. 154(b) by 0 days.

(21) Appl. No.: 16/392,524

(22) Filed: Apr. 23, 2019

(65) Prior Publication Data

US 2019/0247441 A1   Aug. 15, 2019

Related U.S. Application Data

(63) Continuation of application No. 16/391,213, filed on Apr. 22, 2019, now abandoned, which is a continuation-in-part of application No. PCT/KR2018/012664, filed on Oct. 24, 2018.

(30) Foreign Application Priority Data

Oct. 25, 2017 (KR) .................. 10-2017-0139143

(51) Int. Cl.
| | | |
|---|---|---|
| *A61K 35/34* | (2015.01) | |
| *C12N 5/0775* | (2010.01) | |
| *A61P 21/00* | (2006.01) | |
| *A61K 35/32* | (2015.01) | |
| *C12N 5/00* | (2006.01) | |
| *C12N 5/0735* | (2010.01) | |
| *C12N 5/077* | (2010.01) | |
| *C12N 5/074* | (2010.01) | |

(52) U.S. Cl.
CPC .............. *A61K 35/34* (2013.01); *A61K 35/32* (2013.01); *A61P 21/00* (2018.01); *C12N 5/0018* (2013.01); *C12N 5/0606* (2013.01); *C12N 5/066* (2013.01); *C12N 5/0653* (2013.01); *C12N 5/0655* (2013.01); *C12N 5/0662* (2013.01); *C12N 5/0696* (2013.01); *C12N 2501/115* (2013.01); *C12N 2501/15* (2013.01); *C12N 2501/155* (2013.01); *C12N 2501/16* (2013.01); *C12N 2501/235* (2013.01); *C12N 2501/415* (2013.01); *C12N 2501/727* (2013.01); *C12N 2506/02* (2013.01); *C12N 2506/45* (2013.01); *C12N 2533/52* (2013.01); *C12N 2533/54* (2013.01)

(58) Field of Classification Search
CPC ....... A61P 21/00; C12N 5/066; C12N 5/0653; C12N 5/0606; C12N 5/0655; C12N 5/0018; C12N 5/0662; C12N 5/0696; C12N 2501/15; C12N 2533/54; C12N 2506/02; C12N 2501/727; C12N 2501/115; C12N 2501/415; C12N 2506/45; C12N 2501/155; C12N 2501/16; C12N 2501/235; C12N 2533/52; A61K 35/34; A61K 35/32

See application file for complete search history.

(56) References Cited

U.S. PATENT DOCUMENTS

| | | | | |
|---|---|---|---|---|
| 8,017,389 | B2* | 9/2011 | Phillips | C12N 5/0657 424/93.1 |
| 8,883,498 | B2* | 11/2014 | Heike | C12N 5/0658 435/325 |
| 8,883,502 | B2* | 11/2014 | Zhang | C12N 5/0619 435/375 |
| 9,080,147 | B2 | 7/2015 | Pera | |
| 9,752,124 | B2* | 9/2017 | Sato | C12N 5/0671 |
| 2012/0164731 | A1* | 6/2012 | Sakurai | C12N 5/0658 435/377 |
| 2014/0243227 | A1* | 8/2014 | Clevers | C12N 5/067 506/9 |
| 2014/0363405 | A1* | 12/2014 | Cossu | C12N 5/0658 424/93.7 |

FOREIGN PATENT DOCUMENTS

| | | |
|---|---|---|
| KR | 100973324 B | 7/2010 |
| WO | WO-2014161075 A1 | 10/2014 |
| WO | WO-2016055519 A1 | 4/2016 |
| WO | WO-2017026878 A1 | 2/2017 |
| WO | WO-2019083281 A2 | 5/2019 |

OTHER PUBLICATIONS

Hosoyama et al. Derivation of Myogenic Progenitors Directly From Human Pluripotent Stem Cells Using a Sphere-Based Culture. Stem Cells Translationalmedicine 2014;3:564-574. (Year: 2014).*
Kodaka et al. Skeletal Muscle Cell Induction from Pluripotent Stem Cells. Stem Cells International (2017), Article ID 1376151, 16 pages. (Year: 2017).*
Sakurai et al. Paraxial Mesodermal Progenitors Derived from Mouse Embryonic Stem Cells Contribute to Muscle Regeneration via Differentiation into Muscle Satellite Cells. Stem Cells 2008;26:1865-1873. (Year: 2008).*
Shelton et al. Derivation and Expansion of PAX7-Positive Muscle Progenitors from Human and Mouse Embryonic Stem Cells. Stem Cell Reports (2014), 3, 516-529. (Year: 2014).*
Chen et al. Chemically defined conditions for human iPSCSC derivation and culture. Nature Methods (2011), 8(5), 424-429. (Year: 2011).*

(Continued)

*Primary Examiner* — Sean C. Barron
(74) *Attorney, Agent, or Firm* — Sterne, Kessler, Goldstein & Fox P.L.L.C.

(57) ABSTRACT

The present disclosure relates to a novel musculoskeletal stem cell (MSSC) differentiated from an ESC (embryonic stem cell) or an iPSC (induced pluripotent stem cell). The musculoskeletal stem cell of the present disclosure can be easily induced from a human embryonic stem cell or a human-derived pluripotent stem cell and can be effectively differentiated not only into bone but also into cartilage, tendon and muscle. Accordingly, it can be usefully used for prevention or treatment of various musculoskeletal diseases.

28 Claims, 17 Drawing Sheets

(56) References Cited

OTHER PUBLICATIONS

Chal et al. Generation of human muscle fibers and satellite-like cells from human pluripotent stem cells in vitro. Nature Protocols (2016), 11(10), 1833-1850. (Year: 2016).*
Caplan, "Mesenchymal Stem Cells: Time to Change the Name!", Stem Cells Translational Medicine, vol. 6-7 pages (2017).
Chan et al., "Identification of the Human Skeletal Stem Cell", Cell, vol. 175, pp. 43-56 (Sep. 20, 2018).
Rifas, L., "The Role of Noggin in Human Mesenchymal Stem Cell Differentiation," Journal of Cellular Biochemistry 100:824-834, Wiley Online Library, United States (2007).
International Search Report in International Patent Application No. PCT/KR2018012664, dated May 10, 2019, Korean Intellectual Property Office, 7 pages.
Extended European Search Report dated Nov. 15, 2019, in European Patent Application No. 191170901.3, Munich, Germany, European Patent Office, 9 pages.

* cited by examiner

MUSCULOSKELETAL STEM CELL AND MEDIUM FOR INDUCING DIFFERENTIATION OF MUSCULOSKELETAL STEM CELL

CROSS-REFERENCE TO RELATED APPLICATIONS

This patent application is a Continuation of U.S. patent application Ser. No. 16/391,213, filed on Apr. 22, 2019, which is a Continuation-in-part of International Application PCT/KR2018/012664, filed on Oct. 24, 2018, which claims priority to Korean Application 10-2017-0139143, filed on Oct. 25, 2017, each of which is hereby incorporated by reference in its entirety.

BACKGROUND

Field

The present disclosure relates to stem cells and more specifically relates to musculoskeletal stem cells capable of differentiating into musculoskeletal tissues.

Discussion of Related Technology

The disease of the musculoskeletal system made up of muscles, bones, joints, etc. causes severe activity limitation, body pain, etc. The degeneration of the functions of muscles, bones and joints with aging is an unavoidable consequence. The diseases occurring frequently as a result of the degeneration of the function of the musculoskeletal system include degenerative arthritis, tendinitis, bone fracture, sprain, sarcopenia, etc. As life expectancy increases recently due to improvement in health care, the number of patients suffering from musculoskeletal diseases is also increasing. However, quality of life is aggravated because healthy aging with healthy musculoskeletal system is not achieved.

Ossification is the process of bone formation. There are two processes of bone formation: intramembranous ossification and endochondral ossification. Intramembranous ossification is the direct conversion of mesenchymal tissue into bone and occurs inside the skull, while endochondral ossification involves the formation of cartilage tissue from aggregated mesenchymal cells followed by conversion of the cartilage tissue into bone. This ossification process is essential mostly in the bone formation of vertebrates.

Human embryonic stem cells (hESCs) are pluripotent cells that can grow without limitation and can differentiate into any cell type. hESCs are useful tools for the study of embryonic development in cellular level and for the cell replacement therapy. hESCs can differentiate into specific tissues including skeletal tissues such as bone and cartilage and, therefore, may be used for the restoration of skeletal tissues.

Human-induced pluripotent stem cells (hiPSCs) are known as pluripotent stem cells that can differentiate into any type of cells. hiPSCs are useful for the study of embryonic development in cellular level and are drawing attentions as cell therapeutic agents. Because these cells can be differentiated into skeletal tissue, e.g., bone or cartilage, through transplantation, they may be usefully used for the restoration and treatment of damaged skeletal tissue.

Mesenchymal stem cells (MSCs) are the cells that can self-renew and can differentiate into cells of mesenchymal origin such as osteoblasts, adipocytes and cartilage cells. MSCs are used in clinical trials under various conditions and are attempted for trauma, skeletal diseases, graft-versus-host disease following the receipt of bone marrow transplantation, cardiovascular diseases, autoimmune diseases, liver diseases, etc. However, it is very difficult to attain the MSCs in an amount sufficient for therapeutic application. In addition, the mesenchymal stem cells cannot directly differentiate into these tissues in the body in the absence of the in-vitro predifferentiation process of differentiating into bone cartilage or fat using growth factors, vitamins, etc. It is known that the mesenchymal stem cells indirectly facilitate the regeneration of damaged tissues by stimulating intrinsic stem cells by secreting various biofactors, rather than participating directly in the differentiation into mesenchymal tissues including the musculoskeletal tissues (*Stem Cells Transl Med.* 6(6):1445-1451, 2017).

Accordingly, the necessity of researches on cells that can overcome the limitations of mesenchymal stem cells and can differentiate directly into bone, cartilage, ligaments and muscles in the body is increasing.

The foregoing is intended merely to aid in the understanding of the background of the present disclosure and does not constitute admission of prior art.

SUMMARY

One aspect of the invention provides a culture medium composition comprising noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor. The composition may further comprise musculoskeletal stem cells (MSSCs).

The foregoing composition, may further comprise at least one of embryonic stem cells (ESCs) and induced pluripotent stem cells (iPSCs). The composition may further comprise musculoskeletal stem cells (MSSCs).

In the foregoing composition, the Wnt signaling activator may comprise at least one selected from the group consisting of SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), kenpaullone (9-bromo-7,12-dihydro-indolo[3,2-d]-[1]benzazepin-6(5H)-one), CHIR99021 (9-bromo-7,12-dihydro-pyrido[3',2':2,3]azepino[4,5-b]indol-6(5H)-one), CP21R7 (3-(3-amino-phenyl)-4-(1-methyl-1H-indol-3-yl)-pyrrole-2,5-dione), SB203580 (4-(4-fluorophenyl)-2-(4-methylsulfinylphenyl)-5-(4-pyridyl)-1H-imidazole), H-89 (5-isoquinolinesulfonamide), purmorphamine (2-(1-naphthoxy)-6-(4-morpholinoanilino)-9-cyclohexylpurine), and IQ-1 (2-(4-acetyl-phenyl azo)-2-[3,3-dimethyl-3,4-dihydro-2H-isoquinolin-(1E)-ylidene]-acetamide).

In the foregoing composition, the ERK signaling inhibitor may comprise at least one selected from the group consisting of AS703026 (N-[(2S)-2,3-dihydroxypropyl]-3-[(2-fluoro-4-iodophenyl)amino]-isonicotinamide), AZD6244 (6-(4-bromo-2-chloroanilino)-7-fluoro-N-(2-hydroxyethoxy)-3-methylbenzimidazole-5-carbo xamide), PD0325901 (N-[(2R)-2,3-dihydroxypropoxy]-3,4-difluoro-2-[(2-fluoro-4-iodophenyl)amino]-benzamide), ARRY-438162 (5-[(4-bromo-2-fluorophenyl)amino]-4-fluoro-N-(2-hydroxyethoxy)-1-methyl-1H-benzimida zole-6-carboxamide), RDEA119 ((S)—N-(3,4-difluoro-2-((2-fluoro-4-iodophenyl)amino)-6-methoxyphenyl)-1-(2,3-dihydroxypropyl)cyclopropane-1-sulfonamide), GDC0973 ([3,4-difluoro-2-(2-fluoro-4-iodoanilino)phenyl]-3-hydroxy-3-[(2S)-piperidin-2-yl]-azetidin-1-yl-methanone), TAK-733 ((R)-3-(2,3-dihydroxypropyl)-6-fluoro-5-(2- fluoro-4-iodophenyl amino)-8-methylpyrido[2,3-d]pyrimidine-4,7(3H, 8H)-dione), RO5126766 (3-[[3-fluoro-2-(methylsulfamoylamino)-4-pyridyl]methyl]-4-methyl-7-pyrimidin-2-yloxychromen-2-one), and XL-518 ([3,4-difluoro-2-[(2-fluoro-4-iodophenyl)amino]phenyl][3-hydroxy-3-[(2S)-2-piperidinyl]-1-azetidinyl]methanone).

In the foregoing composition, the TGF-β/activin/nodal signaling inhibitor may comprise at least one selected from the group consisting of E-616452 (2-[3-(6-methyl-2-pyridinyl)-1H-pyrazol-4-yl]-1,5-naphthyridine), A-83-01 (3-(6-methyl-2-pyridinyl)-N-phenyl-4-(4-quinolinyl)-1H-pyrazole-1-carbothioamide), and SB431542 (4-[4-(1,3-benzodioxol-5-yl)-5-(2-pyridinyl)-1H-imidazol-2-yl]benzamide).

Another aspect of the invention provides a method of preparing musculoskeletal stem cells (MSSCs) which may comprise culturing cells comprising at least one of ESC (embryonic stem cell) and an iPS (induced pluripotent stem cell) in a foregoing composition.

In the foregoing method, culturing may be performed for at least 5 passes without changing ingredients of the composition. In the method, culturing may be performed for at least 5 passes while maintaining ingredients of noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor of the composition. In the method, culturing may be performed for at least 5 passes while maintaining concentrations of the ingredients.

Another aspect of the invention provides a cell composition comprising musculoskeletal stem cells (MSSCs) having the following characteristics: positive for the ectodermal marker nestin (NES); positive for the myogenic satellite marker Pax7; positive for the mesodermal marker α-SMA; negative for the pluripotency marker LIN28; and negative for the mesenchymal stem cell marker CD90.

In the foregoing cell composition, the MSSCs may further have a characteristic of positive for CD146. The cell composition may further comprise a pharmaceutically acceptable carrier. In the cell composition, at least part of the MSSCs may be suspended in the pharmaceutically acceptable carrier. The cell composition may further comprise a culture medium for culturing mesenchymal stem cells. In the cell composition, the MSSCs may further have at least one of the following characteristics: positive for the pluripotency marker DPPA4; negative for the mesodermal markers T and nodal; positive for the neuroectodermal marker Pax6; positive for the intestinal stem cell marker LGR5; negative for the chondrocyte marker SOX9; negative for the myoblast marker MyoD; positive for CD10; positive for CD44; positive for CD105; positive for CD146; and positive for CD166.

In the foregoing cell composition, the MSSCs may further have a characteristic of negative for CD271. In the cell composition, the MSSCs may be configured to differentiate into mesoderm but not into ectoderm or endoderm. In the cell composition, the MSSCs may be configured to differentiate into muscle, bone, cartilage, tendon or ligament. In the cell composition, the MSSCs may not be configured to differentiate into a nerve cell. In the cell composition, the MSSCs may not be configured to differentiate into an endothelial cell. In the cell composition, the MSSCs may comprise a cell deposited under the accession number KCLRF-BP-00460. The cell composition may further comprise cells differentiated from at least part of the MSSCs, where the differentiated cells comprise cells of muscle, bone, cartilage, tendon or ligament.

Another aspect of the invention provides a method of in vitro differentiation of MSSCs. The method comprises: in vitro culturing, in a culture medium, MSSCs of the cell of one of the foregoing cell compositions; and collecting cells differentiated from at least part of the MSSCs.

In the foregoing method of in vitro differentiation of MSSC, the culture medium may comprise an osteogenic differentiation medium, wherein the collected cells comprise osteoblasts. In the method, the culture medium may comprise an adipogenic differentiation medium, wherein the collected cells comprise adipocytes. In the method, the culture medium may comprise a chondrogenic differentiation medium, wherein the collected cells comprise cartilage cells.

Another aspect of the invention provides a method of preparing musculoskeletal cells. The method comprises: in vitro culturing, in a culture medium, MSSCs of the cell of one of the foregoing cell compositions; and transplanting at least part of the MSSCs into a mass of tissues such that the at least part of the MSSCs differentiate into musculoskeletal cells in the mass of tissues. In the method, the musculoskeletal may comprise at least one of muscle, bone, cartilage, tendon or ligament.

Still another aspect of the invention provides a method of treating a musculoskeletal disease. The method comprises: administering, to a subject in need of such treatment, an effective amount of one of the cell compositions, wherein the musculoskeletal disease may be selected from the group consisting of osteoporosis, osteomalacia, osteogenesis imperfecta, osteopetrosis, osteosclerosis, Paget's disease, bone cancer, arthritis, rickets, fracture, periodontal disease, segmental bone defect, osteolytic bone disease, primary and secondary hyperparathyroidism, hyperostosis, degenerative arthritis, degenerative knee joint disease, degenerative hip joint disease, degenerative foot joint disease, degenerative hand joint disease, degenerative shoulder joint disease, degenerative elbow joint disease, chondromalacia patellae, simple knee arthritis, osteochondritis dissecans, lateral epicondylitis, medial epicondylitis, Heberden's nodes, Bouchard's nodes, degenerative thumb CM arthrosis, meniscal injury, degenerative disc disease, cruciate ligament injury, biceps brachii muscle injury, ligament injury, tendon injury, frozen shoulder, rotator cuff tear, calcific tendinitis, shoulder impingement syndrome, recurrent dislocation, habitual dislocation, senile sarcopenia and muscular dystrophy. In the method, the cell composition may be administered to a portion of the subject's body where the musculoskeletal disease affects.

Still another aspect of the invention provides a method of preparing musculoskeletal stem cells (MSSCs). The method comprises: culturing, in a culture medium composition, cells comprising at least one of ESCs (embryonic stem cells) and an iPSs (induced pluripotent stem cells), wherein the culture medium composition comprises noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor, wherein at least part of the cells are differentiated into MSSCs to provide a cell composition that comprises MSSCs.

In the foregoing method of preparing MSSCs, the cells cultured in the culture medium composition comprise ESCs and does not comprise iPSCs. The cells cultured in the culture medium composition comprise iPSCs and does not comprise ESCs. The cells cultured in the culture medium composition comprise both iPSCs and ESCs. In the method, the Wnt signaling activator may comprise at least one selected from the group consisting of SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), kenpaullone (9-bromo-7,12-dihydro-indolo[3,2-d]-[1]benzazepin-6(5H)-one), CHIR99021 (9-bromo-7,12-dihydropyrido[3',2':2,3]azepino[4,5-b]indol-6(5H)-one), CP21R7 (3-(3-amino-phenyl)-4-(1-methyl-1H-indol-3-yl)-pyrrole-2,5-dione), SB203580 (4-(4-fluorophenyl)-2-(4-methylsulfinylphenyl)-5-(4-pyridyl)-1H-imidazole), H-89 (5-isoquinolinesulfonamide), purmorphamine (2-(1-naphthoxy)-6-(4-morpholinoanilino)-9-cyclohexylpurine), and IQ-1 (2-(4-acetyl-phenylazo)-2-[3,3-dimethyl-3,4-dihydro-2H-isoquinolin-(1E)-ylidene]-acetamide).

In the foregoing method of preparing MSSCs, the ERK signaling inhibitor may comprise at least one selected from the group consisting of AS703026 (N-[(2S)-2,3-dihydroxypropyl]-3-[(2-fluoro-4-iodophenyl)amino]-isonicotinamide), AZD6244 (6-(4-bromo-2-chloroanilino)-7-fluoro-N-(2-hydroxyethoxy)-3-methylbenzimidazole-5-carbo xamide), PD0325901 (N-[(2R)-2,3-dihydroxypropoxy]-3,4-difluoro-2-[(2-fluoro-4-iodophenyl)amino]-benzamide), ARRY-438162 (5-[(4-bromo-2-fluorophenyl)amino]-4-fluoro-N-(2-hydroxyethoxy)-1-methyl-1H-benzimidazole-6-carboxamide), RDEA119 ((S)—N-(3,4-difluoro-2-((2-fluoro-4-iodophenyl)amino)-6-methoxyphenyl)-1-(2,3-dihydroxypropyl)cyclopropane-1-sulfonamide), GDC0973 ([3,4-difluoro-2-(2-fluoro-4-iodoanilino)phenyl]-3-hydroxy-3-[(2S)-piperidin-2-yl]-azetidin-1-yl-methanone), TAK-733 ((R)-3-(2,3-dihydroxypropyl)-6-fluoro-5-(2-fluoro-4-iodophenylamino)-8-methylpyrido[2,3-d]pyrimidine-4,7(3H, 8H)-dione), RO5126766 (3-[[3-fluoro-2-(methylsulfamoylamino)-4-pyridyl]methyl]-4-methyl-7-pyrimidin-2-yloxychromen-2-one), and XL-518 ([3,4-difluoro-2-[(2-fluoro-4-iodophenyl)amino]phenyl][3-hydroxy-3-[(2S)-2-piperidinyl]-1-azetidinyl]methanone).

In the foregoing method of preparing MSSCs, the TGF-β/activin/nodal signaling inhibitor may comprise at least one selected from the group consisting of E-616452 (2-[3-(6-methyl-2-pyridinyl)-1H-pyrazol-4-yl]-1,5-naphthyridine), A-83-01 (3-(6-methyl-2-pyridinyl)-N-phenyl-4-(4-quinolinyl)-1H-pyrazole-1-carbothioamide), and SB431542 (4-[4-(1,3-benzodioxol-5-yl)-5-(2-pyridinyl)-1H-imidazol-2-yl]benzamide). In this method, culturing may be performed for at least 5 passes without changing ingredients of the composition. Culturing may be performed for at least 5 passes while maintaining ingredients of noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor of the composition. Culturing is performed for at least 5 passes while maintaining concentrations of the ingredients.

Still another aspect of the invention provides a method for screening musculoskeletal stem cells (MSSCs). The method comprises: providing cells for screening; and subjecting the cells to a plurality of predetermined tests to determine whether the cells have one or more of the following characteristics: positive for the ectodermal marker nestin (NES), positive for the myogenic satellite marker Pax7, positive for the mesodermal marker α-SMA, negative for the pluripotency marker LIN28, and negative for the mesenchymal stem cell marker CD90. In the method, the cells are determined to be MSSCs when the cells have all of the foregoing characteristics listed in this paragraph.

The method for screening may further comprise determining that the cells are MSSCs when the cells have all of the characteristics. In the method for screening, the plurality of predetermined tests are to determine whether the cells have one or more of the following characteristics: positive for the pluripotency marker DPPA4; negative for the mesodermal markers T and nodal; positive for the neuroectodermal marker Pax6; positive for the intestinal stem cell marker LGR5; negative for the chondrocyte marker SOX9; negative for the myoblast marker MyoD; positive for CD10; positive for CD44; positive for CD105; positive for CD146; and positive for CD166. The method may further comprise determining that the cells are MSSCs when the cells have all of the foregoing characteristics listed in this paragraph. The method may further comprise determining that the cells are MSSCs when the cells have all of the foregoing characteristics listed in this and immediately preceding paragraphs.

DETAILED DESCRIPTION

Stem Cells

Figure 1A:
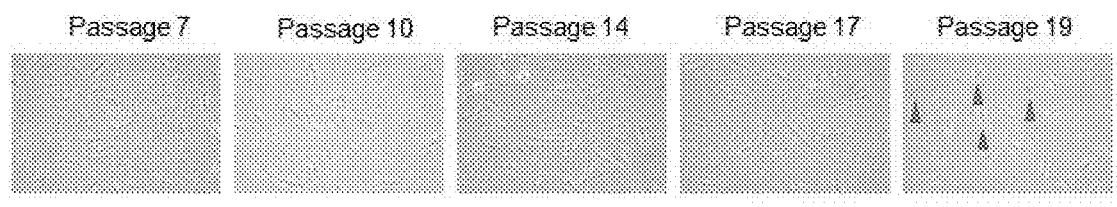
FIGS. 1A-1E show characteristics of hMSSCs differentiated from hESCs according to Example 14.

In the present disclosure, the term "stem cell" refers to an undifferentiated cell capable of differentiating into various body tissues. The stem cells may be classified into totipotent stem cells, pluripotent stem cells, multipotent stem cells, etc. The term stem cell may be used interchangeably with the terms precursor cell, progenitor cell, etc. In the present disclosure, the stem cell may be an embryonic stem cell (ESC), an induced pluripotent stem cell (iPSC) or a mesenchymal stem cell (MSC).

Embryonic Stem Cells

The embryonic stem cell is a pluripotent cell derived from all the three germ layers, having capacity for unlimited proliferation without transformation and self-renewal, although not being limited thereto. The embryonic stem cell or induced pluripotent stem cell used in the present disclosure is derived from human, cow, horse, goat, sheep, dog, cat, mouse, rat, bird, etc., specifically from human.

Musculoskeletal Stem Cells

In the present disclosure, the term "musculoskeletal stem cell (MSSC)" refers to a cell that can differentiate into tissues of bone, cartilage, tendon, ligament or muscle without limitation.

Differentiation

The term "differentiation" refers to the process wherein the structure or function of a cell is specialized while the cell grows through division and proliferation, i.e., the process wherein the form or function changes to perform the task assigned to the cell, tissue, etc. of an organism. In general, it refers to a phenomenon where a relatively simple system is split into two or more qualitatively different subsystems. That is to say, the differentiation refers to the variation of the parts of an initially substantially homogenous biological system or the division to qualitatively different parts or subsystems as a result thereof, for example, the division of head, body, etc. from an initially homogeneous egg during ontogeny.

Inducing Differentiation into Musculoskeletal Stem Cells

According to one aspect of the invention, a musculoskeletal stem cell (MSSC) is differentiated from an embryonic stem cell (ESC) or an induced pluripotent stem cell (iPSC). The musculoskeletal stem cell can further differentiate into bone through endochondral ossification as well as into musculoskeletal tissues such as cartilage, tendon, muscle, ligament, bone, etc.

Medium for Inducing Differentiation of MSSCs from ESCs

In an aspect, the present disclosure provides a medium that induces an embryonic stem cell (ESC) to differentiate into a musculoskeletal stem cell (MSSC). The medium induces a human embryonic stem cell to differentiate into a musculoskeletal stem cell (MSSC). In some examples, the medium contains noggin, leukemia inhibitory factor (LIF), basic fibroblast growth factor (bFGF), Wnt signaling activator, extracellular signal-regulated kinase (ERK) signaling inhibitor and TGF-β/activin/nodal signaling inhibitor. In some examples, the medium contains all six (6) ingredients of noggin, LIF, bFGF, Wnt signaling activator, ERK signaling inhibitor and TGF-β/activin/nodal signaling inhibitor. In other examples, at least one of the six ingredients is absent in the medium.

Medium for Inducing Differentiation of MSSCs from iPSCs

In another aspects, the present disclosure provides a medium that induces an induced pluripotent stem to differentiate into a musculoskeletal stem cell (MSSC). The medium induces a human-derived pluripotent stem cell to differentiate into a musculoskeletal stem cell (MSSC). In some examples, the medium contains noggin, leukemia inhibitory factor (LIF), basic fibroblast growth factor (bFGF), Wnt signaling activator, extracellular signal-regulated kinase (ERK) signaling inhibitor and TGF-β/activin/nodal signaling inhibitor. In some examples, the medium contains the six (6) ingredients of noggin, LIF, bFGF, Wnt signaling activator, ERK signaling inhibitor and TGF-β/activin/nodal signaling inhibitor. In other examples, at least one of the six ingredients is absent in the medium.

Concentration of Noggin

The medium may contain noggin in an amount of about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1150 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450 or 2500 ng/ml. The amount of noggin may be within a range formed by selecting any two numbers (two concentration values) listed in the immediately previous sentence, e.g., between about 150 and about 300 ng/ml, between about 50 and about 500 ng/ml, etc.

Concentration of Noggin Relative to LIF

The medium may contain noggin in an amount of about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1150 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450 or 2500 ng/ml, when the medium contains 20 ng/ml of LIF. When the medium contains 20 ng/ml of LIF, the amount of noggin may be within a range formed by selecting any two numbers (two concentration values) listed in the immediately previous sentence, e.g., between about 150 and about 300 ng/ml, between about 50 and about 500 ng/ml, etc.

Concentration of Leukemia Inhibitory Factor (LIF)

The medium may contain LIF in an amount of about 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 110, 120, 130, 140, 150, 160, 170, 180, 190, 200, 220, 240, 260, 280, 300, or 400 ng/ml, when the medium contains 250 ng/ml of noggin. When the medium contains 250 ng/ml of noggin, the amount of LIF may be within a range formed by selecting any two numbers (two concentration values) listed in the immediately previous sentence, e.g., between about 5 and about 20 ng/ml, between about 10 and about 50 ng/ml, etc.

Concentration of Basic Fibroblast Growth Factor (bFGF)

The medium may contain bFGF in an amount of about 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 320, 340, 360, 380, 400, or 500 ng/ml, when the medium contains 250 ng/ml of noggin. When the medium contains 250 ng/ml of noggin, the amount of bFGF may be within a range formed by selecting any two numbers (two concentration values) listed in the immediately previous sentence, e.g., between about 10 and about 30 ng/ml, between about 20 and about 100 ng/ml, etc.

Wnt Signaling Activator

The Wnt signaling activator may be at least one of SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), kenpaullone (9-bromo-7,12-dihydro-indolo[3,2-d]-[1]benzazepin-6(5H)-one), CHIR99021 (9-bromo-7,12-dihydro-pyrido[3',2':2,3]azepino[4,5-b]indol-6(5H)-one), CP21R7 (3-(3-amino-phenyl)-4-(1-methyl-1H-indol-3-yl)-pyrrole-2,5-dione), SB203580 (4-(4-fluorophenyl)-2-(4-methylsulfinylphenyl)-5-(4-pyridyl)-1H-imidazole), H-89 (5-isoquinolinesulfonamide), purmorphamine (2-(1-naphthoxy)-6-(4-morpholinoanilino)-9-cyclohexylpurine) and IQ-1 (2-(4-acetyl-phenyl azo)-2-[3,3-dimethyl-3,4-dihydro-2H-isoquinolin-(1E)-ylidene]-acetamide), although not being limited thereto.

Concentration of Wnt Signaling Activator

The medium may contain the Wnt signaling activator in an amount of about 100, 120, 140, 160, 180, 200, 220, 240, 260, 280, 300, 320, 340, 360, 380, 400, 420, 440, 460, 480, 500, 600, 700, 800, 900, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7500, 8000, 8500, 9000, 9500, or 10,000 ng/ml, when the medium contains 250 ng/ml of noggin. When the medium contains 250 ng/ml of noggin, the amount of Wnt signaling activator may be within a range formed by selecting any two numbers (two concentration values) listed in the immediately previous sentence, e.g., between about 200 and about 5000 ng/ml, between about 500 and about 2000 ng/ml, etc.

ERK Signaling Inhibitor

The ERK signaling inhibitor may be at least one of AS703026 (N-[(2S)-2,3-dihydroxypropyl]-3-[(2-fluoro-4-iodophenyl)amino]-isonicotinamide), AZD6244 (6-(4-bromo-2-chloroanilino)-7-fluoro-N-(2-hydroxyethoxy)-3-methylbenzimidazole-5-carbo xamide), PD0325901 (N-[(2R)-2,3-dihydroxypropoxy]-3,4-difluoro-2-[(2-fluoro-4-iodophenyl)amino]-benzamide), ARRY-438162 (5-[(4-bromo-2-fluorophenyl)amino]-4-fluoro-N-(2-hydroxyethoxy)-1-methyl-1H-benzimida zole-6-carboxamide), RDEA119 ((S)—N-(3,4-difluoro-2-((2-fluoro-4-iodophenyl)amino)-6-methoxyphenyl)-1-(2,3-dihydroxypropyl)cyclopropane-1-sulfonamide), GDC0973 ([3,4-difluoro-2-(2-fluoro-4-iodoanilino)phenyl]-3-hydroxy-3-[(2S)-piperidin-2-yl]-azetidin-1-yl-methanone), TAK-733 ((R)-3-(2,3-dihydroxypropyl)-6-fluoro-5-(2-fluoro-4-iodophenylamino)-8-methylpyrido[2,3-d]pyrimidine-4,7(3H, 8H)-dione), RO5126766 (3-[[3-fluoro-2-(methylsulfamoylamino)-4-pyridyl]methyl]-4-methyl-7-pyrimidin-2-yloxychromen-2-one) and XL-518 ([3,4-difluoro-2-[(2-fluoro-4-iodophenyl)amino]phenyl][3-hydroxy-3-[(2S)-2-piperidinyl]-1-azetidinyl]methanone), although not being limited thereto.

Concentration of ERK Signaling Inhibitor

The medium may contain the ERK signaling inhibitor in an amount of about 40, 50, 60, 70, 80, 90, 100, 120, 140, 160, 180, 200, 220, 240, 260, 280, 300, 320, 340, 360, 380, 400, 420, 440, 460, 480, 500, 600, 700, 800, 900, 1000, 1100, 1200, 1300, 1400, 1500, 1600, 1700, 1800, 1900, 2000, 2200, 2400, 2600, 2800, 3000, 3200, 3400, 3600, 3800, 4000 4200, 4400, 4600, 4800 or 5000 ng/ml, when the medium contains 250 ng/ml of noggin. When the medium contains 250 ng/ml of noggin, the amount of ERK signaling inhibitor may be within a range formed by selecting any two numbers (two concentration values) listed in the immediately previous sentence, e.g., between about 80 and about 2500 ng/ml, between about 500 and about 1400 ng/ml, etc.

TGF-β/Activin/Nodal Signaling Inhibitor

The TGF-β/activin/nodal signaling inhibitor may be at least one of E-616452 (2-[3-(6-methyl-2-pyridinyl)-1H-pyrazol-4-yl]-1,5-naphthyridine), A-83-01 (3-(6-methyl-2-pyridinyl)-N-phenyl-4-(4-quinolinyl)-1H-pyrazole-1-carbothioamide) and SB431542 (4-[4-1,3-benzodioxol-5-yl)-5-(2-pyridinyl)-1H-imidazol-2-yl]benzamide), although not being limited thereto.

Concentration of TGF-β/Activin/Nodal Signaling Inhibitor

The medium may contain TGF-β/activin/nodal signaling inhibitor in an amount of about 100, 120, 140, 160, 180, 200, 220, 240, 260, 280, 300, 320, 340, 360, 380, 400, 420, 440, 460, 480, 500, 520, 540, 560, 580, 600, 700, 800, 900, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 6000, 7000, 8000, 9000, 10000, 11000, 12000, 13000, 14000, 15000, 16000, 17000, 18000, 19000, 20000, 22000, 24000, 26000, 28000, 30000, 32000, 34000, 36000, 38000 or 40000 ng/ml, when the medium contains 250 ng/ml of noggin. When the medium contains 250 ng/ml of noggin, the amount of TGF-β/activin/nodal inhibitor may be within a range formed by selecting any two numbers (two concentration values) listed in the immediately previous sentence, e.g., between about 300 and about 10000 ng/ml, between about 2000 and about 6000 ng/ml, etc.

For Differentiation into Cartilage or Bone

Figure 7:
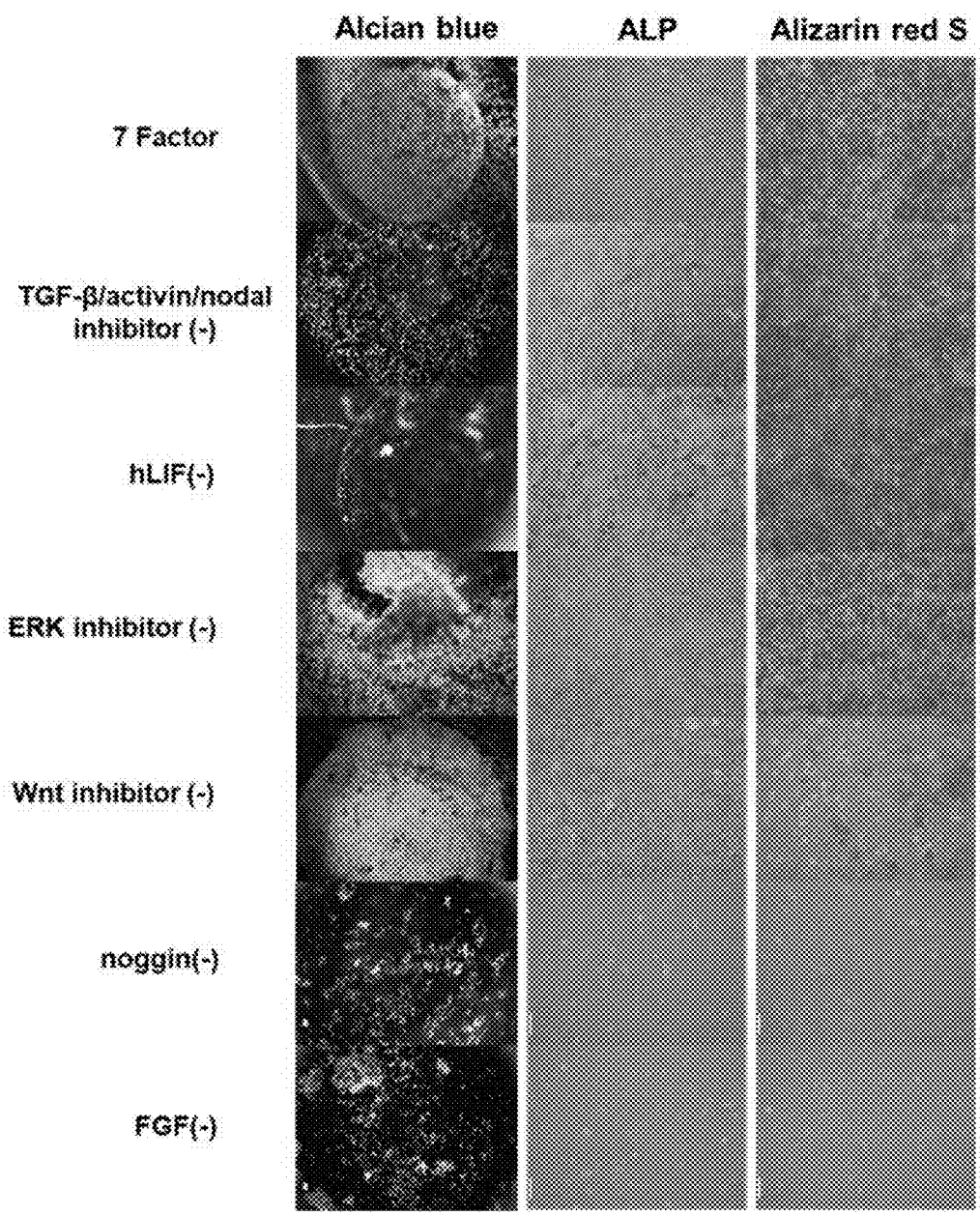
FIG. 7 shows Alcian blue staining for confirming differentiation into cartilage and ALP and Alizarin red S staining for confirming differentiation into bone according to Example 21.

In some examples, the culture medium may contain all of noggin, LIF, bFGF, Wnt signaling activator, ERK signaling inhibitor and TGF-β/activin/nodal signaling inhibitor to provide MSSC that would further differentiate into cartilage (Alcian blue) or bone (ALP and Alizarin red S). See FIG. 7 and Table 3.

Presence of Noggin and Osteogenic Differentiation

Also, when the medium was replaced with one to which a conditioned medium (a culture supernatant obtained after culturing CF1 mouse embryonic fibroblasts with a medium obtained by replacing DMEM/F12 in a complete medium with knockout DMEM (supplemented with 20% knockout serum replacement (Invitrogen, USA), 1 mM glutamine, 1% nonessential amino acids (Invitrogen, USA), 0.1 mM β-mercaptoethanol, 0.1% penicillin-streptomycin and 5 mg/mL bovine serum albumin)) was added in place of noggin and the differentiation capacity was compared, it was confirmed that the medium composition using noggin increased the tendency for osteogenic differentiation 10-fold or higher and increased the differentiation speed by 1-2 weeks (Tables 1 and 2).

Culturing ESCs and iPSCs for Differentiation into MSSCs

In another aspect, the present disclosure provides a method of preparing a musculoskeletal stem cell (MSSC). In some examples, embryonic stem cells (ESCs) are cultured in a medium for inducing differentiation into musculoskeletal stem cells (MSSCs). In other examples, induced pluripotent stem cells (iPSCs) are cultured in a medium for inducing differentiation into musculoskeletal stem cells.

Culturing Passages

Culturing of the stem cells (ESCs and iPSCs) may be performed for at least 5 passes, e.g., 5, 6, 7, 8, 9, 10, 11, 12, 13, 14, 15, 16, 17, 18, 19, 20, 21, 22, 23, 24, 25, 26, 27, 28, 29, 30 or more passages, with or without change of the composition of culture medium. The number of culturing passages may be within a range formed by selecting any two numbers (two concentration values) listed in the immediately previous sentence, e.g., 5-25 passages, 7-18 passages, etc. with or without change of the composition of culture medium.

Composition of Culture Medium in Multiple Passages

The composition of culture medium may be maintained for multiple passages. The composition of culture medium may change but within the concentration ranges of each component disclosed in this application.

Differentiated Stem Cells

In some examples of the present disclosure, musculoskeletal stem cells are differentiated by culturing ESCs or iPSCs for 7 passages or longer in the medium for inducing differentiation into a musculoskeletal stem cell. The musculoskeletal stem cells obtained from 7 passages or more were stably identical. In some examples, they grew with similar morphologies for 10 passages or more, from passage 7 to passage 17, and showed a positive response to staining with the aging marker β-galactosidase since passage 19, suggesting that aging was progressed. FIG. 1A shows cell morphology of hESCs cultured with a medium for inducing differentiation into MSSCs from passage 7 to passage 19.

Characteristics of Resulting MSSCs

In examples, the resulting musculoskeletal stem cells (MSSCs) have at least one of the characteristics listed below.
(a) positive for the ectodermal marker nestin (NES);
(b) positive for the myogenic satellite marker Pax7;

(c) positive for the mesodermal marker α-SMA;
(d) negative for the pluripotency marker LIN28;
(e) negative for the mesenchymal stem cell marker CD90;
(f) positive for CD146;
(g) negative for the mesenchymal stem cell marker CD271;
(h) positive for the pluripotency marker DPPA4;
(i) negative for the mesodermal markers T and nodal;
(j) positive for the neuroectodermal marker Pax6;
(k) positive for the intestinal stem cell marker LGR5;
(l) negative for the chondrocyte marker SOX9;
(m) negative for the myoblast marker MyoD;
(n) positive for CD10;
(o) positive for CD44;
(p) positive for CD105; and
(q) positive for CD166.

MSSC Examples

In one example, the resulting MSSCs have the characteristics of (d)-(g).

In one example, the resulting MSSCs have the characteristics of (a)-(b).

In one example, the resulting MSSCs have the characteristics of (a), (b) and (f).

In one example, the resulting MSSCs have the characteristics of (a)-(c).

In one example, the resulting MSSCs have the characteristics of (a)-(c) and (f).

In one example, the resulting MSSCs have the characteristics of (a)-(d).

In one example, the resulting MSSCs have the characteristics of (a)-(d) and (f).

In one example, the resulting MSSCs have the characteristics of (a)-(e).

In one example, the resulting MSSCs have the characteristics of (a)-(f).

In one example, the resulting MSSCs have the characteristics of (a)-(e) and (g).

In one example, the resulting MSSCs have the characteristics of (a)-(e) and (h).

In one example, the resulting MSSCs have the characteristics of (a)-(e) and (i).

In one example, the resulting MSSCs have the characteristics of (a)-(e) and (j).

In one example, the resulting MSSCs have the characteristics of (a)-(e) and (k).

In one example, the resulting MSSCs have the characteristics of (a)-(e) and (l).

In one example, the resulting MSSCs have the characteristics of (a)-(e) and (m).

In one example, the resulting MSSCs have the characteristics of (a)-(e) and (n).

In one example, the resulting MSSCs have the characteristics of (a)-(e) and (o).

In one example, the resulting MSSCs have the characteristics of (a)-(e) and (p).

In one example, the resulting MSSCs have the characteristics of (a)-(e) and (q).

In one example, the resulting MSSCs have the characteristics of (a)-(g).

In one example, the resulting MSSCs have the characteristics of (a)-(f) and (h).

In one example, the resulting MSSCs have the characteristics of (a)-(f) and (i).

In one example, the resulting MSSCs have the characteristics of (a)-(f) and (j).

In one example, the resulting MSSCs have the characteristics of (a)-(f) and (k).

In one example, the resulting MSSCs have the characteristics of (a)-(f) and (l).

In one example, the resulting MSSCs have the characteristics of (a)-(f) and (m).

In one example, the resulting MSSCs have the characteristics of (a)-(f) and (n).

In one example, the resulting MSSCs have the characteristics of (a)-(f) and (o).

In one example, the resulting MSSCs have the characteristics of (a)-(f) and (p).

In one example, the resulting MSSCs have the characteristics of (a)-(f) and (q).

In one example, the resulting MSSCs have the characteristics of (a)-(h).

In one example, the resulting MSSCs have the characteristics of (a)-(g) and (i).

In one example, the resulting MSSCs have the characteristics of (a)-(g) and (j).

In one example, the resulting MSSCs have the characteristics of (a)-(g) and (k).

In one example, the resulting MSSCs have the characteristics of (a)-(g) and (l).

In one example, the resulting MSSCs have the characteristics of (a)-(g) and (m).

In one example, the resulting MSSCs have the characteristics of (a)-(g) and (n).

In one example, the resulting MSSCs have the characteristics of (a)-(g) and (o).

In one example, the resulting MSSCs have the characteristics of (a)-(g) and (p).

In one example, the resulting MSSCs have the characteristics of (a)-(g) and (q).

In one example, the resulting MSSCs have the characteristics of (a)-(i).

In one example, the resulting MSSCs have the characteristics of (a)-(h) and (j).

In one example, the resulting MSSCs have the characteristics of (a)-(h) and (k).

In one example, the resulting MSSCs have the characteristics of (a)-(h) and (l).

In one example, the resulting MSSCs have the characteristics of (a)-(h) and (m).

In one example, the resulting MSSCs have the characteristics of (a)-(h) and (n).

In one example, the resulting MSSCs have the characteristics of (a)-(h) and (o).

In one example, the resulting MSSCs have the characteristics of (a)-(h) and (p).

In one example, the resulting MSSCs have the characteristics of (a)-(h) and (q).

In one example, the resulting MSSCs have the characteristics of (a)-(j).

In one example, the resulting MSSCs have the characteristics of (a)-(i) and (k).

In one example, the resulting MSSCs have the characteristics of (a)-(i) and (l).

In one example, the resulting MSSCs have the characteristics of (a)-(i) and (m).

In one example, the resulting MSSCs have the characteristics of (a)-(i) and (n).

In one example, the resulting MSSCs have the characteristics of (a)-(i) and (o).

In one example, the resulting MSSCs have the characteristics of (a)-(i) and (p).

In one example, the resulting MSSCs have the characteristics of (a)-(i) and (q).

In one example, the resulting MSSCs have the characteristics of (a)-(k).

In one example, the resulting MSSCs have the characteristics of (a)-(j) and (l).

In one example, the resulting MSSCs have the characteristics of (a)-(j) and (m).

In one example, the resulting MSSCs have the characteristics of (a)-(j) and (n).

In one example, the resulting MSSCs have the characteristics of (a)-(j) and (o).

In one example, the resulting MSSCs have the characteristics of (a)-(j) and (p).

In one example, the resulting MSSCs have the characteristics of (a)-(j) and (q).

In one example, the resulting MSSCs have the characteristics of (a)-(l).

In one example, the resulting MSSCs have the characteristics of (a)-(k) and (m).

In one example, the resulting MSSCs have the characteristics of (a)-(k) and (n).

In one example, the resulting MSSCs have the characteristics of (a)-(k) and (o).

In one example, the resulting MSSCs have the characteristics of (a)-(k) and (p).

In one example, the resulting MSSCs have the characteristics of (a)-(k) and (q).

In one example, the resulting MSSCs have the characteristics of (a)-(m).

In one example, the resulting MSSCs have the characteristics of (a)-(l) and (n).

In one example, the resulting MSSCs have the characteristics of (a)-(l) and (o).

In one example, the resulting MSSCs have the characteristics of (a)-(l) and (p).

In one example, the resulting MSSCs have the characteristics of (a)-(l) and (q).

In one example, the resulting MSSCs have the characteristics of (a)-(n).

In one example, the resulting MSSCs have the characteristics of (a)-(m) and (o).

In one example, the resulting MSSCs have the characteristics of (a)-(m) and (p).

In one example, the resulting MSSCs have the characteristics of (a)-(m) and (q).

In one example, the resulting MSSCs have the characteristics of (a)-(o).

In one example, the resulting MSSCs have the characteristics of (a)-(n) and (p).

In one example, the resulting MSSCs have the characteristics of (a)-(n) and (q).

In one example, the resulting MSSCs have the characteristics of (a)-(p).

In one example, the resulting MSSCs have the characteristics of (a)-(o) and (q).

In one example, the resulting MSSCs have the characteristics of (a)-(q).

Pluripotency Markers and Mesodermal Markers

In an example of the present disclosure, the expression of most pluripotency markers was not observed in the musculoskeletal stem cells of the present disclosure but the expression of DPPA4 was observed and the cells were positive for the ectodermal marker NES. In addition, they were positive for most mesodermal markers except DES and the early mesodermal markers T and nodal and negative for most endodermal markers. See FIG. 1C.

Mesenchymal Stem Cell Markers

In addition, when the expression of mesenchymal stem cell-specific cell surface antigens was investigated for hMSSC, among the mesenchymal stem cell markers, CD44, CD51, CD73, CD105, CD146 and CD166 were expressed in the hMSSCs but CD90 and CD271 were not expressed in the hMSSC. In addition, whereas the vascular cell surface markers CD2, CD3, CD7, CD8, CD11b, CD14, CD19, CD20, CD31, CD34 and CD56 were not expressed, the pre-B cell marker CD10 was expressed. See FIG. 1D.

Tissue-Specific Markers

Additionally, when the expression of various tissue-specific markers was investigated, the mesodermal marker alpha smooth muscle actin (α-SMA), the neuroectodermal marker Pax6, the myogenic satellite marker Pax7, and the intestinal stem cell marker LGR5 were expressed, but the chondrocyte marker SOX9 and the myoblast marker MyoD were not expressed. See FIG. 1E.

hMSSCs Distinguished from Intrinsic Stem Cells

The musculoskeletal stem cells (MSSCs) differentiated from ESCs or iPSCs differ from intrinsic stem cells. It is known that intrinsic stem cells require mesenchymal stem cells' signaling or stimulation to differentiate into musculoskeletal tissues. Chan, C. K., et al. (2018). Identification of the Human Skeletal Stem Cell, *Cell*, 175, 43-56. However, MSSCs differentiated from ESCs or iPSCs do not need such signaling or stimulation by mesenchymal stem cells for the differentiation into musculoskeletal tissues. Further, it is also known that the intrinsic stem cells show negative for CD146; however, the MSSCs differentiated from ESCs or iPSCs show positive for CD 146.

Differentiation into Musculoskeletal Cells

The musculoskeletal stem cells differentiated from ESCs or iPSCs are capable of being differentiated into the mesoderm but not into the ectoderm or endoderm. The musculoskeletal stem cells differentiated from ESCs or iPSCs are also capable of being differentiated into musculoskeletal cells in vitro and in vivo. The musculoskeletal stem cells may be differentiated into cells of muscle, bone, cartilage, tendon or ligament in vivo and in vitro.

In vitro Differentiation of MSSCs into Skeletal Muscle Cells

Figure 2A:
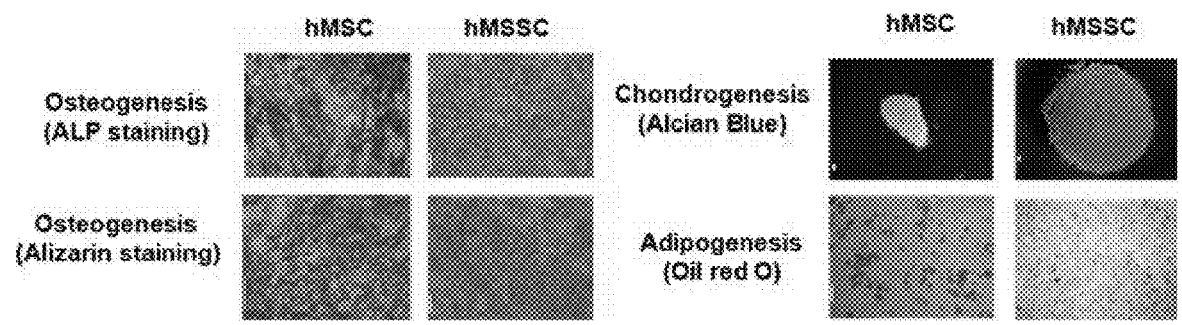
FIGS. 2A-2E show in-vitro differentiation capacity of hMSSCs according to Examples 15.1-15.4.
Figure 2B:
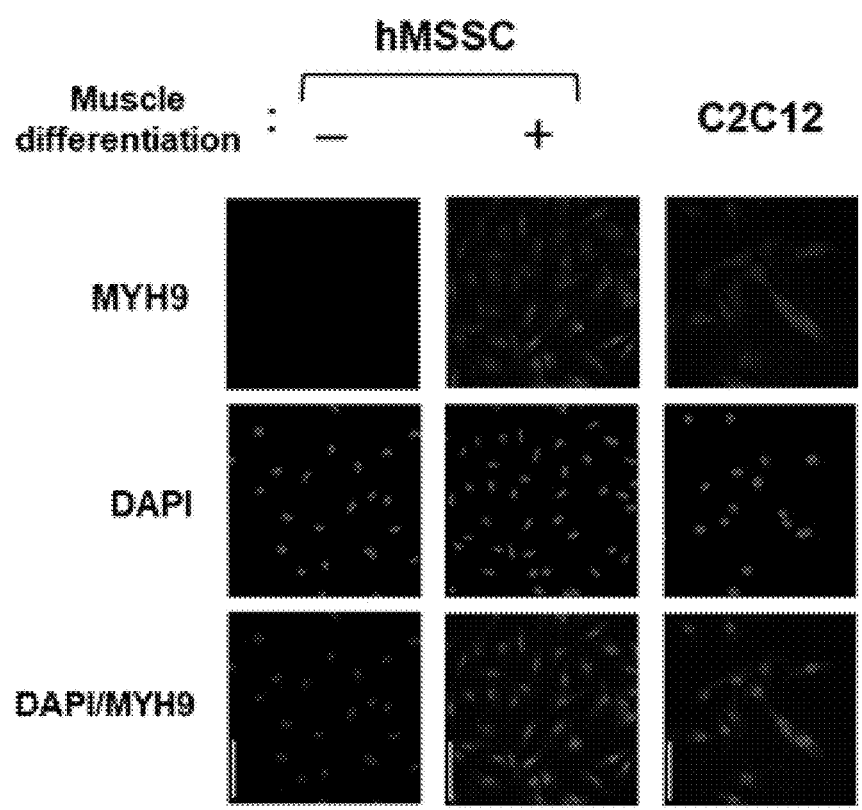

FIG. 2A shows a result of comparing the in-vitro bone, cartilage and fat differentiation capacity of hMSCs and hMSSCs. FIG. 2B shows a result of confirming that hMSSCs has the potential to differentiate into skeletal muscle by immunocytochemistry for the skeletal muscle cell-specific marker MYH9. C2C12 was used as a positive control group for the skeletal muscle cell.

Not Differentiating into Endothelial Cells

Figure 2C:
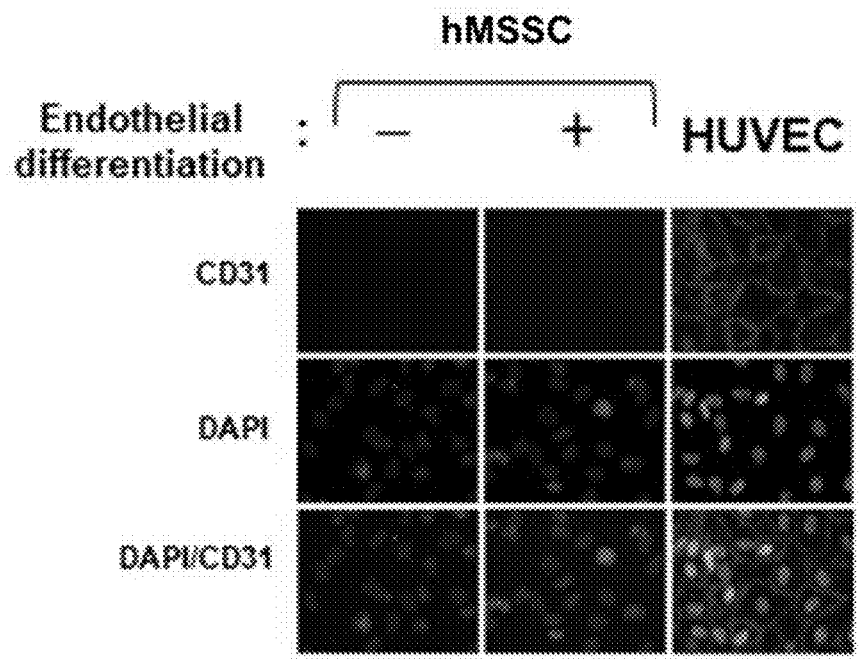
Figure 2D:
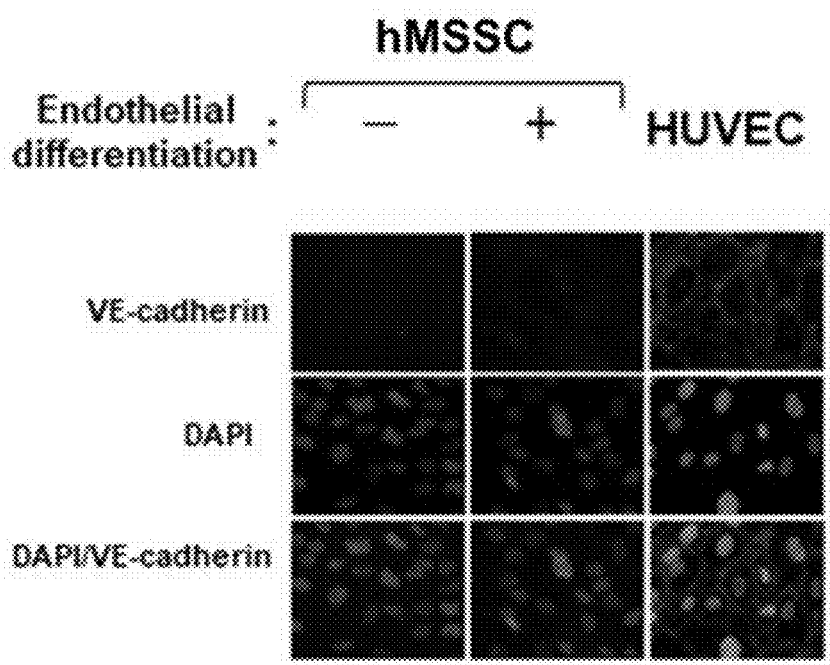

In some examples, the MSSCs differentiated from ESCs or iPSCs do not have the potential to differentiate into endothelial cells even if placed in a medium for inducing differentiation into an EC (endothelial growth medium). FIGS. 2C and 2D confirm that hMSSCs did not differentiate into endothelial cells by immunocytochemistry for the endothelial cell-specific markers CD31 and VE-cadherin.

Not Differentiating into Nerve Cells

Figure 2E:
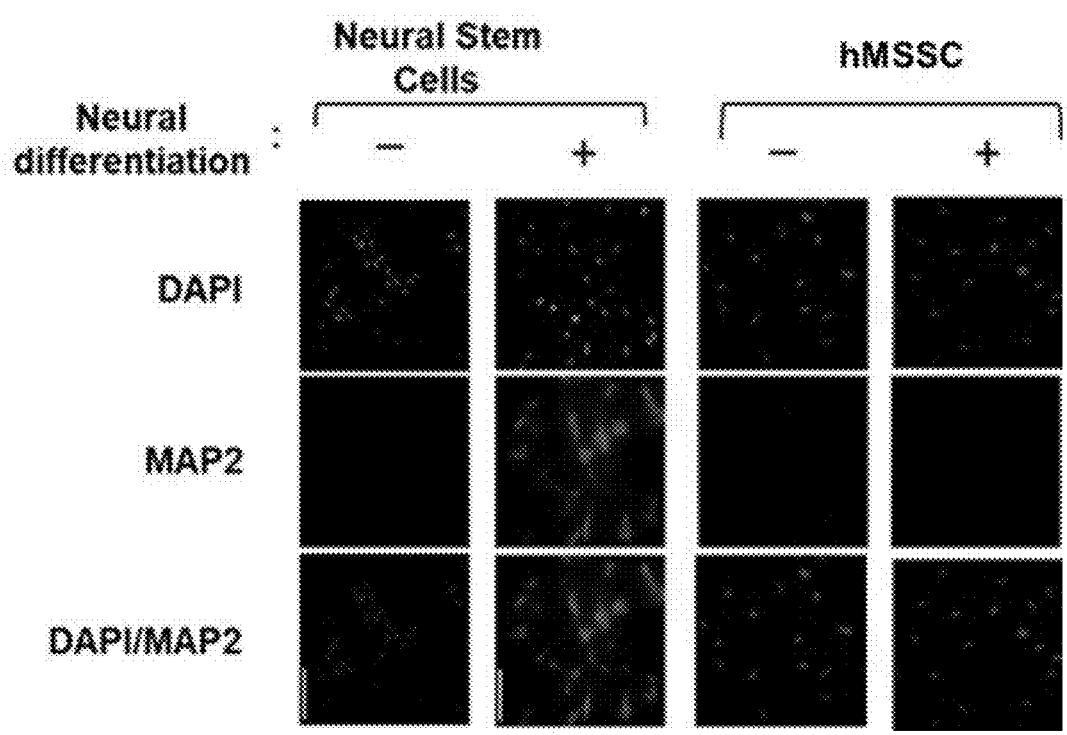

In some examples, the MSSCs differentiated from ESCs or iPSCs do not have the potential to differentiate into nerve cells even if placed in a medium for inducing differentiation into nerve cells. FIG. 2E confirms that hMSSCs did not differentiate into nerve cells by immunocytochemistry for the nerve cell-specific marker MAP2. As a positive control group, neural stem cells differentiated from H9 hESCs were used.

Culturing MSSCs

The MSSCs differentiated from ESCs or iPSCs may be further cultured in a medium. The culture medium may include any medium for culturing mesenchymal stem cells, including MSCGM, MSCGM-CD, etc.

Transplanting MSSCs for In Vivo Differentiation

In one aspect of the present disclosure, the MSSCs are transplanted into a mass of certain tissues or an organ to the formation of musculoskeletal cells in the body of tissues or the organ. In some examples, the MSSCs are transplanted into kidney capsule or hypoderm for the formation of muscle, fat, tendon, bone and cartilage cells. In some examples, the MSSCs are cultured in a medium for culturing mesenchymal stem cells prior to transplanting.

In vivo Differentiation into Muscle, Fat and Tendon Cells

Figure 3A:
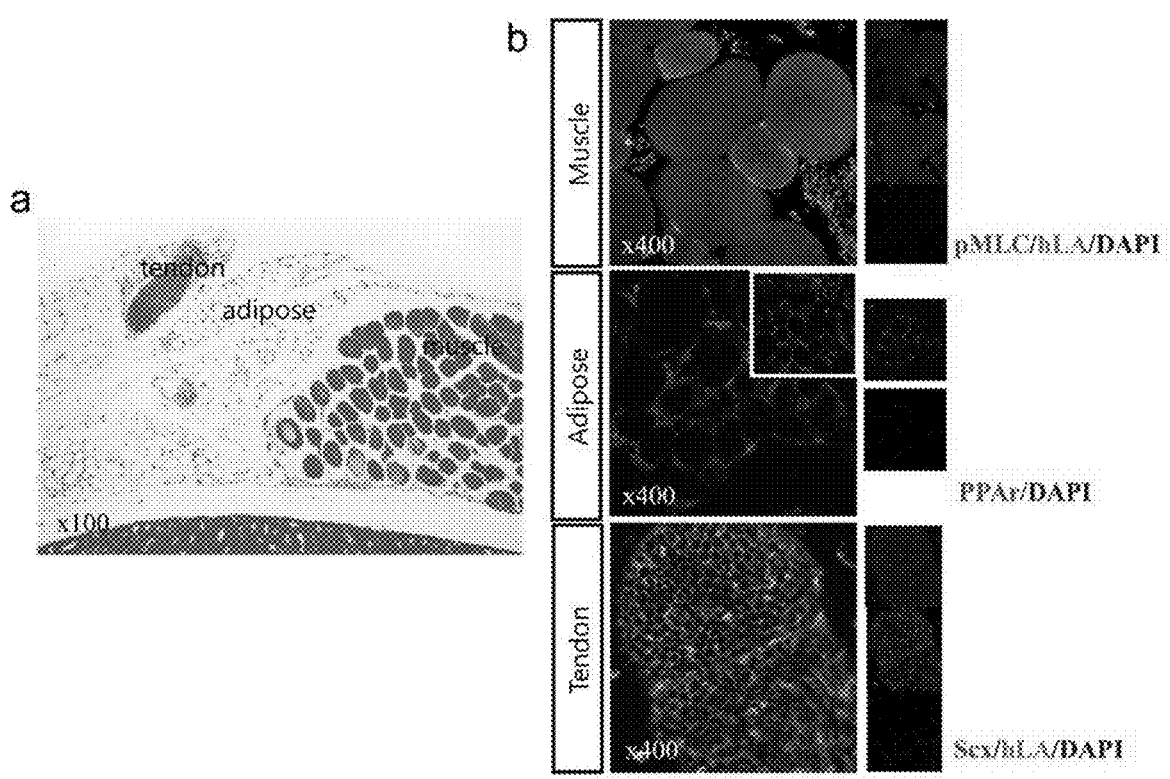
FIGS. 3A-3C show differentiability of hMSSCs in vivo according to Example 16.

In FIG. 3A, (a) shows that muscle, fat and tendon cells were formed by transplanting of hMSSCs into kidney as confirmed by H&E staining. In FIG. 3A, (b) shows the differentiation of hMSSCs in kidney into muscle, fat and tendon cells by immunohistochemistry for the muscle-specific marker pMLC, the fat-specific marker PPARgamma (PPAr) and ligament-specific marker Scx. hLA is a human cell-specific marker, and the staining result shows that the cell is derived from human. The differentiated muscle cells were skeletal muscle cells and not smooth muscle cells. It was also confirmed in the in-vivo experiment that they could be differentiated into fat, although the differentiation into fat was not observed in the in-vitro experiment.

In Vivo Differentiation into Bone Cells

Figure 3B:
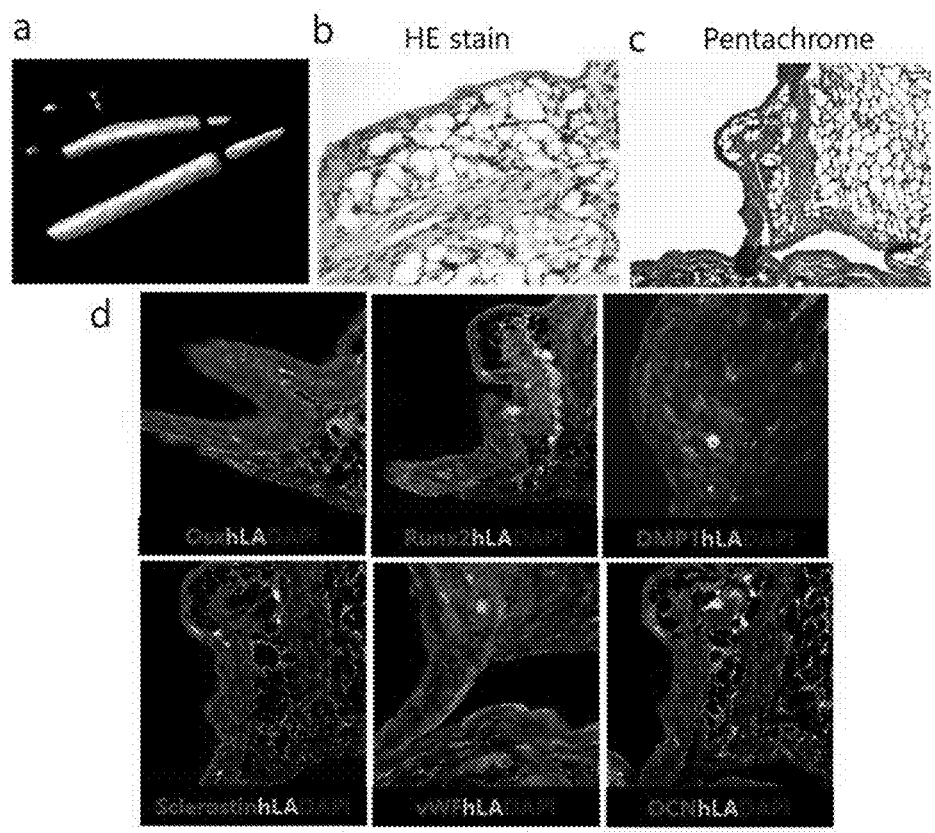

In FIG. 3B, (a) is a micro-CT scanning result confirming that bone was formed by transplanting hMSSCs into the kidney. In FIG. 3B, (b) and (c) show the formation of bone by H&E and pentachrome immunohistochemical staining. In FIG. 3B, (d) shows the expression of the human cell marker hLA (human leukocyte antigen), the bone markers Osx (osterix), Runx2, DMP1 and OCN (osteocalin) and the vascular marker vWF in the cells of the osteoblastic tissue by immunohistochemistry.

In Vivo Differentiation into Cartilage Cells

Figure 3C:
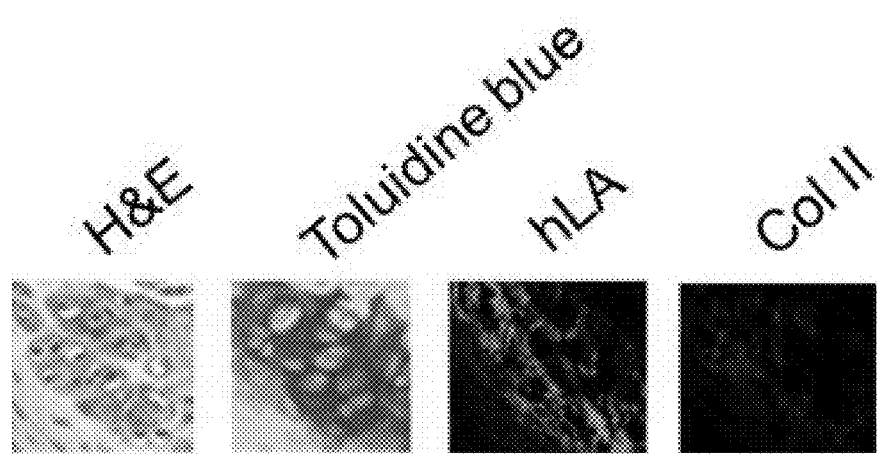

FIG. 3C shows that cartilage cells were formed by transplanting hMSSCs into the hypoderm by H&E and toluidine blue immunohistochemical staining. The expression of the cartilage marker ColII (collagen II) was also confirmed by immunohistochemistry.

Not Differentiating into Nerve Cells

The MSSCs differentiated from ESCs or iPSCs may not have the potential for differentiating into nerve cells even if placed in a medium for inducing differentiation into nerve cells. FIG. 2E confirms that hMSSCs did not differentiate into nerve cells by immunocytochemistry for the nerve cell-specific marker MAP2. As a positive control group, neural stem cells differentiated from H9 hESCs were used.

Not Differentiating into Endothelial Cells

The MSSCs differentiated from ESCs or iPSCs may not have the potential for differentiating into endothelial cells even if placed in a medium for inducing differentiation into an EC (endothelial growth medium). FIGS. 2C and 2D confirm that hMSSCs did not differentiate into endothelial cells by immunocytochemistry for the endothelial cell-specific markers CD31 and VE-cadherin.

Deposit of Musculoskeletal Stem Cells

The musculoskeletal stem cell was deposited in the Korean Cell Line Bank on Oct. 10, 2018 and was given the accession number KCLRF-BP-00460.

Pharmaceutical Composition or Therapeutic Agent

The MSSCs differentiated from ESCs or iPSCs may be used to provide a pharmaceutical composition or therapeutic agent for preventing or treating a musculoskeletal disease. The pharmaceutical composition contains an effective amount of the MSSCs differentiated from ESCs or iPSCs.

Musculoskeletal Disease

The pharmaceutical composition may be applicable for treatment or prevention of one or more diseases selected from a group consisting of osteoporosis, osteomalacia, osteogenesis imperfecta, osteopetrosis, osteosclerosis, Paget's disease, bone cancer, arthritis, rickets, fracture, periodontal disease, segmental bone defect, osteolytic bone disease, primary and secondary hyperparathyroidism, hyperostosis, degenerative arthritis, degenerative knee joint disease, degenerative hip joint disease, degenerative foot joint disease, degenerative hand joint disease, degenerative shoulder joint disease, degenerative elbow joint disease, chondromalacia patellae, simple knee arthritis, osteochondritis dissecans, lateral epicondylitis, medial epicondylitis, Heberden's nodes, Bouchard's nodes, degenerative thumb CM arthrosis, meniscal injury, degenerative disc disease, cruciate ligament injury, biceps brachii muscle injury, ligament injury, tendon injury, frozen shoulder, rotator cuff tear, calcific tendinitis, shoulder impingement syndrome, recurrent dislocation, habitual dislocation, senile sarcopenia and muscular dystrophy, although not being limited thereto.

Pharmaceutically Acceptable Carrier

The pharmaceutical composition may contain one or more pharmaceutically acceptable carriers. For example, the one or more pharmaceutically acceptable carriers are selected from the group consisting of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto.

Other Components

The pharmaceutical composition may further contain at least one of a lubricant, a humectant, a sweetener, a flavorant, an emulsifier, a suspending agent, a preservative, etc., in addition to the MSSCs and pharmaceutically acceptable carrier.

Administration

The pharmaceutical composition containing the MSSCs may be administered for treatment or prevention of a musculoskeletal disease. The pharmaceutical composition of the present disclosure may be administered orally or parenterally. For parenteral administration, it may be administered via intravenous injection, subcutaneous injection, intramuscular injection, intraarticular injection, intraosseous infusion, intraperitoneal injection, endothelial administration, topical administration, intranasal administration, intrapulmonary administration, intrarectal administration, etc. Also, the composition may be administered by any device capable of delivering the active ingredient to a target cell.

Dosage

The pharmaceutical composition containing the MSSCs is administered in an amount effective of the MSSCs for treatment or prevention of a musculoskeletal disease. The effective amount or an appropriate administration dosage may be determined in consideration of various factors such as formulation method, administration mode, the age, body weight and sex of a patient, pathological condition, diet, administration time, administration route, excretion rate and response sensitivity. The administration dosage may be about $10^2$, $10^3$, $10^4$, $10^5$, $10^6$, $10^7$, $10^8$, $10^9$, $10^{10}$, $10^{11}$ or $10^{12}$ cells/kg for an adult. The dosage may be within a range formed by selecting any two numbers (two concentration values) listed in the immediately previous sentence, e.g., about $10^2$ to about $10^{10}$, about $10^4$ to about $10^7$ cells/kg for an adult.

Formulation

The pharmaceutical composition containing the MSSCs may be prepared into a single-dose unit or multiple-dose unit formulation using a pharmaceutically acceptable carrier and/or excipient according to a method that can be easily carried out by those skilled in the art. The formulation may be in the form of a solution in an oily or aqueous medium, a suspension, a syrup, an emulsion, an extract, a powder, a granule, a tablet or a capsule and may further contain a dispersant or a stabilizer. In addition, the composition may be administered either independently or in combination with other therapeutic agent(s) and they may be administered either sequentially or simultaneously. Also, it may be administered as a single dose or repeatedly as desired.

Cell Therapeutic Agent

In the present disclosure, the term "cell therapeutic agent" refers to medication used for therapeutic, diagnostic and preventive purposes, which contains a cell or tissue isolated from human and cultured and prepared through special operation (as provided by the USFDA). It is a medication used for therapeutic, diagnostic and preventive purposes through a series of actions of in-vitro multiplication and screening of living autologous, allogenic and xenogenic cells or changing of the biological characteristics of cells by other means for recovering the functions of cells or tissues.

Prevention and Treatment

In the present disclosure, the term "prevention" refers to any action of inhibiting a musculoskeletal disease or delaying the progression thereof by administering the composition or cell therapeutic agent of the present disclosure. In the present disclosure, the term "treatment" refers to any action of improving or favorably changing a musculoskeletal disease by administering the composition or cell therapeutic agent of the present disclosure.

For Human and Animal

The pharmaceutical composition or cell therapeutic agent of the present disclosure may be used for human or an animal.

Used Alone or in Combination with Other Treatment

The pharmaceutical composition or cell therapeutic agent of the present disclosure may be used either alone or in combination with surgery, radiotherapy, hormone therapy, chemotherapy, a biological response modifier, implantation, insertion of an artificial joint, artificial cartilage, etc., regeneration therapy, etc., for prevention and treatment of a musculoskeletal disease.

Method of Screening MSSCs

In another aspect, the present disclosure provides a method of screening or identifying a musculoskeletal stem cell based on characteristics of the MSSCs differentiated from ESCs and/or iPSCs. In examples, cells having at least one of the following characteristics listed below may be determined as MSSCs:

(a) positive for the ectodermal marker nestin (NES);
(b) positive for the myogenic satellite marker Pax7;
(c) positive for the mesodermal marker α-SMA;
(d) negative for the pluripotency marker LIN28;
(e) negative for the mesenchymal stem cell marker CD90;
(f) positive for CD146;
(g) negative for the mesenchymal stem cell marker CD271;
(h) positive for the pluripotency marker DPPA4;
(i) negative for the mesodermal markers T and nodal;
(j) positive for the neuroectodermal marker Pax6;
(k) positive for the intestinal stem cell marker LGR5;
(l) negative for the chondrocyte marker SOX9;
(m) negative for the myoblast marker MyoD;
(n) positive for CD10;
(o) positive for CD44;
(p) positive for CD105; and
(q) positive for CD166.

MSSC Examples

Cells having the characteristics of (d)-(g) may be identified as MSSCs.

Cells having the characteristics of (a)-(b) may be identified as MSSCs.

Cells having the characteristics of (a), (b) and (f) may be identified as MSSCs.

Cells having the characteristics of (a)-(c) may be identified as MSSCs.

Cells having the characteristics of (a)-(c) and (f) may be identified as MSSCs.

Cells having the characteristics of (a)-(d) may be identified as MSSCs.

Cells having the characteristics of (a)-(d) and (f) may be identified as MSSCs.

Cells having the characteristics of (a)-(e) may be identified as MSSCs.

Cells having the characteristics of (a)-(f) may be identified as MSSCs.

Cells having the characteristics of (a)-(e) and (g) may be identified as MSSCs.

Cells having the characteristics of (a)-(e) and (h) may be identified as MSSCs.

Cells having the characteristics of (a)-(e) and (i) may be identified as MSSCs.

Cells having the characteristics of (a)-(e) and (j) may be identified as MSSCs.

Cells having the characteristics of (a)-(e) and (k) may be identified as MSSCs.

Cells having the characteristics of (a)-(e) and (l) may be identified as MSSCs.

Cells having the characteristics of (a)-(e) and (m) may be identified as MSSCs.

Cells having the characteristics of (a)-(e) and (n) may be identified as MSSCs.

Cells having the characteristics of (a)-(e) and (o) may be identified as MSSCs.

Cells having the characteristics of (a)-(e) and (p) may be identified as MSSCs.

Cells having the characteristics of (a)-(e) and (q) may be identified as MSSCs.

Cells having the characteristics of (a)-(g) may be identified as MSSCs.

Cells having the characteristics of (a)-(f) and (h) may be identified as MSSCs.

Cells having the characteristics of (a)-(f) and (i) may be identified as MSSCs.

Cells having the characteristics of (a)-(f) and (j) may be identified as MSSCs.

Cells having the characteristics of (a)-(f) and (k) may be identified as MSSCs.

Cells having the characteristics of (a)-(f) and (l) may be identified as MSSCs.

Cells having the characteristics of (a)-(f) and (m) may be identified as MSSCs.

Cells having the characteristics of (a)-(f) and (n) may be identified as MSSCs.

Cells having the characteristics of (a)-(f) and (o) may be identified as MSSCs.

Cells having the characteristics of (a)-(f) and (p) may be identified as MSSCs.

Cells having the characteristics of (a)-(f) and (q) may be identified as MSSCs.

Cells having the characteristics of (a)-(h) may be identified as MSSCs.
Cells having the characteristics of (a)-(g) and (i) may be identified as MSSCs.
Cells having the characteristics of (a)-(g) and (j) may be identified as MSSCs.
Cells having the characteristics of (a)-(g) and (k) may be identified as MSSCs.
Cells having the characteristics of (a)-(g) and (l) may be identified as MSSCs.
Cells having the characteristics of (a)-(g) and (m) may be identified as MSSCs.
Cells having the characteristics of (a)-(g) and (n) may be identified as MSSCs.
Cells having the characteristics of (a)-(g) and (o) may be identified as MSSCs.
Cells having the characteristics of (a)-(g) and (p) may be identified as MSSCs.
Cells having the characteristics of (a)-(g) and (q) may be identified as MSSCs.
Cells having the characteristics of (a)-(i) may be identified as MSSCs.
Cells having the characteristics of (a)-(h) and (j) may be identified as MSSCs.
Cells having the characteristics of (a)-(h) and (k) may be identified as MSSCs.
Cells having the characteristics of (a)-(h) and (l) may be identified as MSSCs.
Cells having the characteristics of (a)-(h) and (m) may be identified as MSSCs.
Cells having the characteristics of (a)-(h) and (n) may be identified as MSSCs.
Cells having the characteristics of (a)-(h) and (o) may be identified as MSSCs.
Cells having the characteristics of (a)-(h) and (p) may be identified as MSSCs.
Cells having the characteristics of (a)-(h) and (q) may be identified as MSSCs.
Cells having the characteristics of (a)-(j) may be identified as MSSCs.
Cells having the characteristics of (a)-(i) and (k) may be identified as MSSCs.
Cells having the characteristics of (a)-(i) and (l) may be identified as MSSCs.
Cells having the characteristics of (a)-(i) and (m) may be identified as MSSCs.
Cells having the characteristics of (a)-(i) and (n) may be identified as MSSCs.
Cells having the characteristics of (a)-(i) and (o) may be identified as MSSCs.
Cells having the characteristics of (a)-(i) and (p) may be identified as MSSCs.
Cells having the characteristics of (a)-(i) and (q) may be identified as MSSCs.
Cells having the characteristics of (a)-(k) may be identified as MSSCs.
Cells having the characteristics of (a)-(j) and (l) may be identified as MSSCs.
Cells having the characteristics of (a)-(j) and (m) may be identified as MSSCs.
Cells having the characteristics of (a)-(j) and (n) may be identified as MSSCs.
Cells having the characteristics of (a)-(j) and (o) may be identified as MSSCs.
Cells having the characteristics of (a)-(j) and (p) may be identified as MSSCs.
Cells having the characteristics of (a)-(j) and (q) may be identified as MSSCs.
Cells having the characteristics of (a)-(l) may be identified as MSSCs.
Cells having the characteristics of (a)-(k) and (m) may be identified as MSSCs.
Cells having the characteristics of (a)-(k) and (n) may be identified as MSSCs.
Cells having the characteristics of (a)-(k) and (o) may be identified as MSSCs.
Cells having the characteristics of (a)-(k) and (p) may be identified as MSSCs.
Cells having the characteristics of (a)-(k) and (q) may be identified as MSSCs.
Cells having the characteristics of (a)-(m) may be identified as MSSCs.
Cells having the characteristics of (a)-(l) and (n) may be identified as MSSCs.
Cells having the characteristics of (a)-(l) and (o) may be identified as MSSCs.
Cells having the characteristics of (a)-(l) and (p) may be identified as MSSCs.
Cells having the characteristics of (a)-(l) and (q) may be identified as MSSCs.
Cells having the characteristics of (a)-(n) may be identified as MSSCs.
Cells having the characteristics of (a)-(m) and (o) may be identified as MSSCs.
Cells having the characteristics of (a)-(m) and (p) may be identified as MSSCs.
Cells having the characteristics of (a)-(m) and (q) may be identified as MSSCs.
Cells having the characteristics of (a)-(o) may be identified as MSSCs.
Cells having the characteristics of (a)-(n) and (p) may be identified as MSSCs.
Cells having the characteristics of (a)-(n) and (q) may be identified as MSSCs.
Cells having the characteristics of (a)-(p) may be identified as MSSCs.
Cells having the characteristics of (a)-(o) and (q) may be identified as MSSCs.
Cells having the characteristics of (a)-(q) may be identified as MSSCs.

Additional Markers for Screening MSSCs

In addition to the characteristics listed in the immediately foregoing paragraph, a cell having one or more additional ones of the following characteristics may be determined as MSSCs:
- negative for the mesenchymal stem cell marker CD271;
- positive for the pluripotency marker DPPA4;
- negative for the mesodermal markers T and nodal;
- positive for the neuroectodermal marker Pax6;
- positive for the intestinal stem cell marker LGR5;
- negative for the chondrocyte marker SOX9;
- negative for the myoblast marker MyoD;
- positive for one or more of CD10, CD44, CD105, CD146 and CD166.

EXAMPLES

The present disclosure will be further discussed in terms of examples. However, the following examples are for illustrative purposes only, and it will be apparent to those of ordinary skill in the art that the scope of the present disclosure is not limited to the examples.

Example 1. Experimental Animals 7- to 10-week-old Balb/c-nude background mice (weighing 20-24 g) were purchased from Orient Bio (Seongnam, Korea). All animal experiments were performed according to the guidelines of the Chonbuk University Animal Care and Use Committee. The animals were accommodated under controlled-temperature (21-24° C.) and 12:12-hr light-dark cycle environments and were given free access to water and feed.

Example 2.1.1. Pre-Culturing hESCs

H9 hESCs (human embryonic stem cells) were purchased from WiCell (Madison, Mich., USA). A hESC culture medium was prepared as DMEM/F12 (Invitrogen, USA) supplemented with 20% knockout serum replacement (KSR; Invitrogen, USA), 1 mM glutamine (Invitrogen, USA), 1% nonessential amino acids (Invitrogen, USA), 0.1 mM β-mercaptoethanol (Invitrogen, USA), 0.1% penicillin/streptomycin (Invitrogen, USA) and 15 ng/mL bFGF (R&D Systems, USA). The hESCs were cultured with the prepared hESC culture medium on CF1 mouse embryonic fibroblast (MEF) feeder cells whose cell division was blocked by mitomycin C treatment.

Example 2.1.2. Induction of Differentiation from hESCs into hMSSCs

A medium for inducing differentiation into MSSCs (hereinafter referred to as "MSSC medium") was prepared with the following composition:
1) 250 ng/mL human noggin (KOMA Biotech, Korea),
2) 20 ng/mL human LIF (KOMA Biotech, Korea),
3) 15 ng/mL basic fibroblast growth factor b(FGF) (R&D Systems, USA) (FGF2 signaling activator),
4) 3 μM (1,396 ng/ml) CHIR99021 (molecular weight 465.34, Cayman, USA) (Wnt signaling activator), 5) 1 μM (482.19 ng/ml) PD0325901 (molecular weight 482.19, Cayman, USA) (ERK (extracellular signal-regulated kinase) signaling inhibitor), and 6) 10 μM (3,843.9 ng/ml) SB431542 (molecular weight 384.39, Tocris, United Kingdom) (TGF-β/activin/nodal signaling inhibitor).

The medium further contained 10% knockout serum replacement (Invitrogen, USA), 1% N2 supplement (Gibco, USA), 2% B27 supplement (Gibco, USA), 1% nonessential amino acids (Gibco, USA), 43% DMEM/F12 (Gibco, USA), 43% Neurobasal (Gibco, USA), 1 mM glutamine, 0.1 mM β-mercaptoethanol, 0.1% penicillin-streptomycin and 5 mg/mL bovine serum albumin (Gibco, USA).

The hESCs from Example 2.1.1 were treated with ROCK (Rho-associated coiled-coil kinase) inhibitor (Y-27632, 10 μM, Calbiochem, Germany) and PKC (protein kinase C) inhibitor (Go6983, 2.5 μM, Sigma, USA) for 24 hours in order to enhance survivability. Then, hESCs were trypsinized by treating with TrypLE (Life Technologies, USA). Subsequently, the trypsinized hESCs were induced to differentiate into hMSSCs by culturing with the MSSC medium on a culture dish coated with vitronectin and gelatin (1 ng/mL, Sigma, USA) until passage 7. The differentiated MSSC cells were identified to be stably identical from passage 5 and the cells cultured for 10 passages were deposited in the Korean Cell Line Bank on Oct. 10, 2018 and were given the accession number KCLRF-BP-00460.

Example 2.1.3. Induction of Differentiation from hESCs into hMSSCs

The experiment of Example 2.1.2 is repeated except that the MSSC medium contains 1 ng/mL human LIF instead of 20 ng/ml.

Example 2.1.4. Induction of Differentiation from hESCs into hMSSCs

The experiment of Example 2.1.2 is repeated except that the MSSC medium contains 5 ng/mL human LIF instead of 20 ng/ml.

Example 2.1.5. Induction of Differentiation from hESCs into hMSSCs

The experiment of Example 2.1.2 is repeated except that the MSSC medium contains 50 ng/mL human LIF instead of 20 ng/ml.

Example 2.1.6. Induction of Differentiation from hESCs into hMSSCs

The experiment of Example 2.1.2 is repeated except that the MSSC medium contains 100 ng/mL human LIF instead of 20 ng/ml.

Example 2.1.7. Induction of Differentiation from hESCs into hMSSCs

The experiment of Example 2.1.2 is repeated except that the MSSC medium contains 1 ng/mL bFGF instead of 15 ng/ml.

Example 2.1.8. Induction of Differentiation from hESCs into hMSSCs

The experiment of Example 2.1.2 is repeated except that the MSSC medium contains 500 ng/mL bFGF instead of 15 ng/ml.

Example 2.1.9. Induction of Differentiation from hESCs into hMSSCs

The experiment of Example 2.1.2 is repeated except that the MSSC medium contains 100 ng/mL bFGF instead of 15 ng/ml.

Example 2.1.10. Induction of Differentiation from hESCs into hMSSCs

The experiment of Example 2.1.2 is repeated except that the MSSC medium contains 200 ng/mL bFGF instead of 15 ng/ml.

Example 2.1.11. Induction of Differentiation from hESCs into hMSSCs

The experiment of Example 2.1.2 is repeated except that the MSSC medium contains 100 ng/mL Wnt signaling activator instead of 1,396 ng/ml.

Example 2.1.12. Induction of Differentiation from hESCs into hMSSCs

The experiment of Example 2.1.2 is repeated except that the MSSC medium contains 200 ng/mL Wnt signaling activator instead of 1,396 ng/ml.

Example 2.1.13. Induction of Differentiation from hESCs into hMSSCs

The experiment of Example 2.1.2 is repeated except that the MSSC medium contains 5,000 ng/mL Wnt signaling activator instead of 1,396 ng/ml.

Example 2.1.14. Induction of Differentiation from hESCs into hMSSCs

The experiment of Example 2.1.2 is repeated except that the MSSC medium contains 10,000 ng/mL Wnt signaling activator instead of 1,396 ng/ml.

Example 2.1.15. Induction of Differentiation from hESCs into hMSSCs

The experiment of Example 2.1.2 is repeated except that the MSSC medium contains 40 ng/mL ERK signaling inhibitor instead of 482.19 ng/ml.

Example 2.1.16. Induction of Differentiation from hESCs into hMSSCs

The experiment of Example 2.1.2 is repeated except that the MSSC medium contains 80 ng/mL ERK signaling inhibitor instead of 482.19 ng/ml.

Example 2.1.17. Induction of Differentiation from hESCs into hMSSCs

The experiment of Example 2.1.2 is repeated except that the MSSC medium contains 2,500 ng/mL ERK signaling inhibitor instead of 482.19 ng/ml.

Example 2.1.18. Induction of Differentiation from hESCs into hMSSCs

The experiment of Example 2.1.2 is repeated except that the MSSC medium contains 5,000 ng/mL ERK signaling inhibitor instead of 482.19 ng/ml.

Example 2.1.19. Induction of Differentiation from hESCs into hMSSCs

The experiment of Example 2.1.2 is repeated except that the MSSC medium contains 100 ng/mL TGF-β/activin/nodal signaling inhibitor instead of 3,843.9 ng/ml.

Example 2.1.20. Induction of Differentiation from hESCs into hMSSCs

The experiment of Example 2.1.2 is repeated except that the MSSC medium contains 300 ng/mL TGF-β/activin/nodal signaling inhibitor instead of 3,843.9 ng/ml.

Example 2.1.21. Induction of Differentiation from hESCs into hMSSCs

The experiment of Example 2.1.2 is repeated except that the MSSC medium contains 10,000 ng/mL TGF-β/activin/nodal signaling inhibitor instead of 3,843.9 ng/ml.

Example 2.1.22. Induction of Differentiation from hESCs into hMSSCs

The experiment of Example 2.1.2 is repeated except that the MSSC medium contains 40,000 ng/mL TGF-β/activin/nodal signaling inhibitor instead of 3,843.9 ng/ml.

Example 2.1.23. Induction of Differentiation from hESCs into hMSSCs

Examples 2.1.2 through Example 2.1.22 are repeated except that the MSSC medium contains 25 ng/mL human noggin instead of 250 ng/ml.

Example 2.1.24. Induction of Differentiation from hESCs into hMSSCs

Examples 2.1.2 through Example 2.1.22 are repeated except that the MSSC medium contains 50 ng/mL human noggin instead of 250 ng/ml.

Example 2.1.25. Induction of Differentiation from hESCs into hMSSCs

Examples 2.1.2 through Example 2.1.22 are repeated except that the MSSC medium contains 500 ng/mL human noggin instead of 250 ng/ml.

Example 2.1.26. Induction of Differentiation from hESCs into hMSSCs

Examples 2.1.2 through Example 2.1.22 are repeated except that the MSSC medium contains 2,500 ng/mL human noggin instead of 250 ng/ml.

Example 2.2.1. Pre-Culturing hiPSCs hiPSCs (human induced pluripotent stem cells) were obtained by introducing the OCT4, KLF4, SOX2 and cMYC genes to BJ fibroblasts (ATCC®CRL2522™) using Sendai virus according to the method developed by Hasegawa et al. (Fusaki et al., 2009, PNAS 85, 348-362). A hiPSC culture medium was prepared as DMEM/F12 (Invitrogen, USA) supplemented with 20% knockout serum replacement (KSR; Invitrogen, USA), 1 mM glutamine (Invitrogen, USA), 1% nonessential amino acids (Invitrogen, USA), 0.1 mM β-mercaptoethanol (Invitrogen, USA), 0.1% penicillin/streptomycin (Invitrogen, USA) and 15 ng/mL bFGF (R&D Systems, USA). The hiPSCs were cultured with the prepared hiPSC culture medium on CF1 mouse embryonic fibroblast (MEF) feeder cells whose cell division was blocked by mitomycin C treatment.

Example 2.2.2. Induction of Differentiation from hiPSCs into hMSSCs

A medium for inducing differentiation into MSSCs (hereinafter, referred to as "MSSC medium") was prepared with the following composition:
1) 250 ng/mL human noggin (KOMA Biotech, Korea),
2) 20 ng/mL human LIF (KOMA Biotech, Korea),
3) 15 ng/mL basic fibroblast growth factor (FGF) (R&D Systems, USA) (FGF2 signaling activator), 4) 3 µM (1,396 ng/ml) CHIR99021 (molecular weight 465.34, Cayman, USA) (Wnt signaling activator), 5) 1 µM (482.19 ng/ml) PD0325901 (molecular weight 482.19, Cayman, USA) (ERK (extracellular signal-regulated kinase) signaling inhibitor), 6) 10 µM (3,843.9 ng/ml) SB431542 (molecular weight 384.39, Tocris, United Kingdom) (TGF-β/activin/nodal signaling inhibitor), and 7) 10% knockout serum replacement (Invitrogen, USA), 1% N2 supplement (Gibco, USA), 2% B27 supplement (Gibco, USA), 1% nonessential amino acids (Gibco, USA), 43% DMEM/F12 (Gibco, USA), 43% Neurobasal (Gibco, USA), 1 mM glutamine, 0.1 mM β-mercaptoethanol, 0.1% penicillin-streptomycin and 5 mg/mL bovine serum albumin (Gibco, USA).

The hiPSCs from Example 2.2.1 were treated with ROCK (Rho-associated coiled-coil kinase) inhibitor (Y-27632, 10 µM, Calbiochem, Germany) and PKC (protein kinase C) inhibitor (Go6983, 2.5 µM, Sigma, USA) for 24 hours in order to enhance survivability. Then, the hiPSCs were trypsinized by treating with TrypLE (Life Technologies, USA). Subsequently, the trypsinized hiPSCs were induced to differentiate into hMSSCs by culturing with the MSSC medium on a culture dish coated with vitronectin and gelatin (1 ng/mL, Sigma, USA) until passage 7. The differentiated MSSC cells were identified to be stably identical from passage 5.

Example 2.2.3. Induction of Differentiation from hiPSCs into hMSSCs

The experiment of Example 2.2.2 is repeated except that the MSSC medium contains 1 ng/mL human LIF instead of 20 ng/ml.

Example 2.2.4. Induction of Differentiation from hiPSCs into hMSSCs

The experiment of Example 2.2.2 is repeated except that the MSSC medium contains 5 ng/mL human LIF instead of 20 ng/ml.

Example 2.2.5. Induction of Differentiation from hiPSCs into hMSSCs

The experiment of Example 2.2.2 is repeated except that the MSSC medium contains 50 ng/mL human LIF instead of 20 ng/ml.

Example 2.2.6. Induction of Differentiation from hiPSCs into hMSSCs

The experiment of Example 2.2.2 is repeated except that the MSSC medium contains 100 ng/mL human LIF instead of 20 ng/ml.

Example 2.2.7. Induction of Differentiation from hiPSCs into hMSSCs

The experiment of Example 2.2.2 is repeated except that the MSSC medium contains 1 ng/mL bFGF instead of 15 ng/ml.

Example 2.2.8. Induction of Differentiation from hiPSCs into hMSSCs

The experiment of Example 2.2.2 is repeated except that the MSSC medium contains 500 ng/mL bFGF instead of 15 ng/ml.

Example 2.2.9. Induction of Differentiation from hiPSCs into hMSSCs

The experiment of Example 2.2.2 is repeated except that the MSSC medium contains 100 ng/mL bFGF instead of 15 ng/ml.

Example 2.2.10. Induction of Differentiation from hiPSCs into hMSSCs

The experiment of Example 2.2.2 is repeated except that the MSSC medium contains 200 ng/mL bFGF instead of 15 ng/ml.

Example 2.2.11. Induction of Differentiation from hiPSCs into hMSSCs

The experiment of Example 2.2.2 is repeated except that the MSSC medium contains 100 ng/mL Wnt signaling activator instead of 1,396 ng/ml.

Example 2.2.12. Induction of Differentiation from hiPSCs into hMSSCs

The experiment of Example 2.2.2 is repeated except that the MSSC medium contains 200 ng/mL Wnt signaling activator instead of 1,396 ng/ml.

Example 2.2.13. Induction of Differentiation from hiPSCs into hMSSCs

The experiment of Example 2.2.2 is repeated except that the MSSC medium contains 5,000 ng/mL Wnt signaling activator instead of 1,396 ng/ml.

Example 2.2.14. Induction of Differentiation from hiPSCs into hMSSCs

The experiment of Example 2.2.2 is repeated except that the MSSC medium contains 10,000 ng/mL Wnt signaling activator instead of 1,396 ng/ml.

Example 2.2.15. Induction of Differentiation from hiPSCs into hMSSCs

The experiment of Example 2.2.2 is repeated except that the MSSC medium contains 40 ng/mL ERK signaling inhibitor instead of 482.19 ng/ml.

Example 2.2.16. Induction of Differentiation from hiPSCs into hMSSCs

The experiment of Example 2.2.2 is repeated except that the MSSC medium contains 80 ng/mL ERK signaling inhibitor instead of 482.19 ng/ml.

Example 2.2.17. Induction of Differentiation from hiPSCs into hMSSCs

The experiment of Example 2.2.2 is repeated except that the MSSC medium contains 2,500 ng/mL ERK signaling inhibitor instead of 482.19 ng/ml.

Example 2.2.18. Induction of Differentiation from hiPSCs into hMSSCs

The experiment of Example 2.2.2 is repeated except that the MSSC medium contains 5,000 ng/mL ERK signaling inhibitor instead of 482.19 ng/ml.

Example 2.2.19. Induction of Differentiation from hiPSCs into hMSSCs

The experiment of Example 2.2.2 is repeated except that the MSSC medium contains 100 ng/mL TGF-β/activin/nodal signaling inhibitor instead of 3,843.9 ng/ml.

Example 2.2.20. Induction of Differentiation from hiPSCs into hMSSCs

The experiment of Example 2.2.2 is repeated except that the MSSC medium contains 300 ng/mL TGF-β/activin/nodal signaling inhibitor instead of 3,843.9 ng/ml.

Example 2.2.21. Induction of Differentiation from hiPSCs into hMSSCs

The experiment of Example 2.2.2 is repeated except that the MSSC medium contains 10,000 ng/mL TGF-β/activin/nodal signaling inhibitor instead of 3,843.9 ng/ml.

Example 2.2.22. Induction of Differentiation from hiPSCs into hMSSCs

The experiment of Example 2.2.2 is repeated except that the MSSC medium contains 40,000 ng/mL TGF-β/activin/nodal signaling inhibitor instead of 3,843.9 ng/ml.

Example 2.2.23. Induction of Differentiation from hiPSCs into hMSSCs

Examples 2.2.2 through Example 2.2.22 are repeated except that the MSSC medium contains 25 ng/mL human noggin instead of 250 ng/ml.

Example 2.2.24. Induction of Differentiation from hiPSCs into hMSSCs

Examples 2.2.2 through Example 2.2.22 are repeated except that the MSSC medium contains 50 ng/mL human noggin instead of 250 ng/ml.

Example 2.2.25. Induction of Differentiation from hiPSCs into hMSSCs

Examples 2.2.2 through Example 2.2.22 are repeated except that the MSSC medium contains 500 ng/mL human noggin instead of 250 ng/ml.

Example 2.2.26. Induction of Differentiation from hiPSCs into hMSSCs

Examples 2.2.2 through Example 2.2.22 are repeated except that the MSSC medium contains 2,500 ng/mL human noggin instead of 250 ng/ml.

Example 3.1. Immunohistochemistry

Samples obtained by injecting the hMSSCs differentiated in Example 2.1.2 into the hypoderm and kidney of Balb/c-nude as described in Examples 10.1 and 10.2 were fixed overnight at 4° C. in 2% paraformaldehyde (PFA; Wako, Japan). For a sample to investigate differentiation into bone, decalcification was conducted at 4° C. for 2 weeks in PBS (pH 7.2) using 0.4 M EDTA. Then, the samples were dehydrated using ethanol and xylene sequentially, embedded in paraffin and cut to 5 μm thickness. The cut surface was stained with H&E and modified Movat's pentachrome (Cosmobio, Japan).

Example 3.2. Immunohistochemistry

Example 3.1 is repeated for the hMSSCs differentiated in Examples 2.1.3-2.1.26 and Examples 2.2.3-2.2.26.

Example 4.1. RNA Sequencing

RNAs were extracted from H9 hESCs, human mesenchymal stem cells (hMSCs; Lonza, Switzerland) and the hMSSCs of Example 2.1.2 using Trizol reagent (Invitrogen, USA). The RNA quality was evaluated with the Agilent 2100 bioanalyzer and the RNA 6000 Nano Chip (Agilent Technologies, USA) and quantification was performed using the ND-2000 spectrophotometer (Thermo Inc., USA). An RNA library for RNA sequencing was established using the SENSE 3' mRNA-Seq Library Prep Kit (Lexogen Inc., Australia). RNA sequencing was conducted using NextSeq 500 (Illumina Inc., USA). The SENSE 3' mRNA-Seq reads were aligned using Bowtie2 version 2.1.0. The difference in gene expression was determined using Bioconductor R version 3.2.2 with EdgeR. The read count data were processed with Genowiz version 4.0.5.6 (Ocium Biosolutions, USA).

Example 4.2. RNA Sequencing

Example 4.1 is repeated for the hMSSCs differentiated in Examples 2.1.3-2.1.26 and Examples 2.2.3-2.2.26.

Example 5.1. Immunochemistry

"Immunocytochemistry" was performed. For immunofluorescence staining, the cells were fixed in 4% paraformaldehyde, made permeable with 0.5% Triton X-100 and then blocked with 10% normal goat, normal rabbit or fetal bovine serum in phosphate-buffered saline (PBS). The sample was stained overnight at 4° C. with primary antibodies against Tuj1 (Covance, USA), α-smooth muscle (α-SMA, Sigma, USA), Nanog (Santa Cruz, USA), Oct3/4 (Santa Cruz, USA), Sox2 (Santa Cruz, USA), CD31 (DAKO, Japan), vascular endothelial-cadherin (R&D, USA), MYH9 (Santa Cruz, USA), HNK-1 (Santa Cruz, USA) and MAP-2 (Santa Cruz, USA). Then, the cells were stained with the secondary antibodies Alexa Fluor 488-goat anti-mouse IgG, Alexa Fluor 594-donkey anti-rabbit IgG, Alexa Fluor 488-donkey anti-rabbit IgG and Alexa Fluor 594-donkey anti-mouse IgG (Invitrogen, USA). Then, the cell nuclei were stained with DAPI (4,6-diamidino-2-phenylindole). Then, images were obtained using the Olympus IX71 optical microscope and the MetaMorph software (Molecular Devices, USA).

"Immunohistochemistry" was performed. Tissues were fixed overnight at 4° C. with 4% PFA (Wako, Japan) in PBS. All samples were decalcified with Morse's solution. The samples were dehydrated sequentially with ethanol and xylene, embedded in paraffin (Leica Biosystems, Germany) and then cut to 5 μm thickness. After blocking the cut surface for 15 minutes in 3% hydrogen peroxide, the samples were incubated at 4° C. overnight with primary antibodies. The primary antibodies treated on the cut surface are as follows: mouse monoclonal antibody against HLA class I (Abcam, United Kingdom), goat polyclonal antibody against collagen type II (Santacruz, USA), rabbit polyclonal antibody against osteocalcin (Santacruz, USA), osterix (Abcam, USA), phospho-myosin light chain (pMLC) (Abcam, USA), scleraxis (Antibodies Online, USA), PPARgamma (PPAr) (Santacruz, USA) Runx2 (Novus, USA), DMP1 (Santacruz, USA), vWF (Santacruz, USA) and sclerostin (Santacruz, USA). The used secondary antibodies were Alexa 555 (Invitrogen, USA) and Alexa 488 (Invitrogen, USA) IgG. The immunostained cut surface was counterstained with TO-PRO3 (Invitrogen, USA) to visualize the nuclei. The fluorescence-labeled cut surface was imaged with the Leica DM 5000 microscope (Leica Microsystems, Germany) or a confocal microscope (LSM510; Carl Zeiss, Germany) and analyzed with the Zen software.

Example 5.2. Immunochemistry

Example 5.1 is repeated for the hMSSCs differentiated in Examples 2.1.3-2.1.26 and Examples 2.2.3-2.2.26.

Example 6.1. Flow Cytometry

After separating the hMSSCs of Examples 2.1 and 2.2 into a single cell suspension by treating with trypsin/EDTA and blocking nonspecific binding with 2% BSA in PBS, the cells were contacted with monoclonal antibodies against Sca, CD2, CD3, CD4, CD7, CD8, CD10, CD11b, CD14, CD19, CD20, CD31, CD34, CD44, CD45, CD51, CD56, CD73, CD90, CD105, CD146, CD166, CD235a and CD271 (BD Biosciences, USA) in a buffer solution [1×PBS, 1% BSA and 0.01% sodium azide] and then washed. The cells were contacted with Alexa Fluor 488 secondary mouse-IgGs (Invitrogen, USA), washed and then analyzed using a flow cytometer (FACStar Plus Flowcytometer, BD Biosciences, USA). Normal mouse IgGs (BD Biosciences, USA) were used as negative control group.

Example 6.2. Flow Cytometry

Example 6.1 is repeated for the hMSSCs differentiated in Examples 2.1.3-2.1.26 and Examples 2.2.3-2.2.26.

Example 7.1.1. Differentiation of Human Mesenchymal Stem Cells (hMSCs) and hMSSCs into Osteoblast In Vitro In order to differentiate the hMSSCs of Examples 2.1.2 and 2.2.2 into osteoblasts, the cells were cultured in an osteogenic differentiation medium (StemPro® osteogenic differentiation kit, Life Technologies, USA) under the condition of 37° C. and 5% $CO_2$ for 14 days. Alkaline phosphatase (Roche, Switzerland) staining and alizarin red S (Sigma, USA) staining were conducted to observe osteogenesis. The differentiation of hMSCs (Lonza, Switzerland) into osteoblasts was also compared in the same manner.

Example 7.1.2. Differentiation of hMSSCs into Osteoblast In Vitro

Example 7.1.1 is repeated for the hMSSCs differentiated in Examples 2.1.3-2.1.26 and Examples 2.2.3-2.2.26.

Example 7.2.1. Differentiation of Human Mesenchymal Stem Cells (hMCS) and hMSSCS into Adipocyte In Vitro In order to differentiate the hMSSCs of Examples 2.1.2 and 2.2.2 into adipocytes, the cells were cultured in an adipogenic differentiation medium (StemPro® adipogenic differentiation kit, Life Technologies, USA) under the condition of 37° C. and 5% $CO_2$ for 14 days. Oil red O (Sigma, USA) staining was conducted to observe adipogenesis. The differentiation of hMSCs (Lonza, Switzerland) into adipocytes was also compared in the same manner.

Example 7.2.2. Differentiation of hMSSCs into Adipocyte In Vitro

Example 7.2.1 is repeated for the hMSSCs differentiated in Examples 2.1.3-2.1.26 and Examples 2.2.3-2.2.26.

Example 7.3.1. Differentiation of Human Mesenchymal Stem Cell (hMSCs) and hMSSCs into Cartilage Cell In Vitro In order to differentiate the hMSSCs of Examples 2.1.2 and 2.2.2 into cartilage cells, the cells were resuspended in a chondrogenic differentiation medium (StemPro® chondrogenic differentiation kit, Life Technologies, USA) and then centrifuged. For formation of micromass, the formed pellets were resuspended in a differentiation medium to $1 \times 10^5/\mu L$ and then 5 μL of the cell solution was dropped at the center of a 96-well plate. After incubating the micromass for 2 hours under a high-humidity condition and adding a heated chondrogenic differentiation medium, incubation was performed in an incubator under the condition of 5% $CO_2$ and 37° C. The culture medium was re-feeded with 3- to 4-day intervals. 14 days later, the chondrogenic pellets were stained with Alcian blue. The differentiation of hMSCs (Lonza, Switzerland) into cartilage cells was also compared in the same manner.

Example 7.3.2. Differentiation of hMSSCs into Cartilage Cell In Vitro

Example 7.3.1 is repeated for the hMSSCs differentiated in Examples 2.1.3-2.1.26 and Examples 2.2.3-2.2.26.

Example 8.1.1. Differentiation Capacity of hMSSCs into Endothelial Cell In Vitro It was investigated whether the hMSSCs of Example 2.1.2 were differentiated into endothelial cells (ECs). The hMSSCs were differentiated by culturing with a medium for inducing differentiation into an EC (endothelial growth medium (EGM)-2 (Lonza, Walkersville, Md., USA) supplemented with 50 ng/mL VEGF (vascular endothelial growth factor: ProSpec, Rehovot, Israel) and 10 ng/mL bFGF (basic fibroblast growth factor; ProSpec, Rehovot, Israel) for 6 days. The differentiation was confirmed by immunocytochemistry.

Example 8.1.2. Differentiation Capacity of hMSSCs into Endothelial Cell In Vitro Example 8.1.1 is repeated for the hMSSCs differentiated in Examples 2.1.3-2.1.26 and Examples 2.2.3-2.2.26.

Example 8.2.1. Differentiation Capacity of hMSSCs into Skeletal Muscle Cell In Vitro It was investigated whether the hMSSCs of Examples 2.1.2 and 2.2.2 were differentiated into skeletal muscle cells. The hMSSCs were differentiated by culturing with a skeletal muscle differentiation medium (DMEM supplemented with 2% B27) for 2 weeks on a Matrigel-coated cover slip. The differentiation was confirmed by immunocytochemistry.

Example 8.2.2. Differentiation Capacity of hMSSCs into Skeletal Muscle Cell In Vitro Example 8.2.1 is repeated for the hMSSCs differentiated in Examples 2.1.3-2.1.26 and Examples 2.2.3-2.2.26.

Example 9.1. Induction of Differentiation from hMSSCs to Nerve Cell In Vitro For differentiation into nerve cells, the hMSSCs of Example 2.1.2 were plated on a polyornithine- and laminin-coated culture dish. 2 days later, the culture medium was exchanged with a medium for inducing differentiation into a nerve (Neurobasal medium containing 2% B27, 2 mM GlutaMAX and antibiotics). From day 7, 0.5 mM dibutyl cAMP (Sigma, USA) was added every day for 3 days. As a control group, human neural stem cells differentiated from H9 hESCs (Gibco, USA) were differentiated into nerve cells in the same manner. The differentiation was confirmed by immunocytochemistry.

Example 9.2. Induction of Differentiation from hMSSCs to Nerve Cell In Vitro Example 9.1 is repeated for the hMSSCs differentiated in Examples 2.1.3-2.1.26 and Examples 2.2.3-2.2.26.

Example 10.1.1. Differentiation Capacity of hMSSCs in Mouse Kidney

In order to measure the differentiation capacity of the hMSSCs of Example 2.1.2 in mouse kidney, the hMSSCs were cultured with a MSCGM-CD (Lonza, Switzerland) medium for 2-5 passages and the hMSSCs ($2 \times 10^5$ cells) were cultured in an agarose gel well with DMEM+20% FBS for 2 days to form cell aggregates, which were transplanted into the kidney capsule of Balb/c nude mouse. Immunohistochemistry and immunohistochemical staining were performed 4 weeks after the transplantation.

Example 10.1.2. Differentiation Capacity of hMSSCs in Mouse Kidney

Example 10.1.1 is repeated for the hMSSCs differentiated in Examples 2.1.3-2.1.26 and Examples 2.2.3-2.2.26.

Example 10.2.1. Differentiation Capacity of hMSSCs in Mouse Hypoderm

In order to measure the differentiation capacity of the hMSSCs of Example 2.1.2 in mouse hypoderm, the hMSSCs were cultured with a MSCGM-CD (Lonza, Switzerland) medium for 2-5 passages and the hMSSCs ($2 \times 10^5$ cells) were loaded in fibrin glue (Greenplast®, Green Cross, Korea) to which 1 µg/mL hyaluronic acid (Sigma, USA) was added and then transplanted into the hypoderm of Balb/c nude mouse. Immunohistochemistry and immunohistochemical staining were performed 4 weeks after the transplantation.

Example 10.2.2. Differentiation Capacity of hMSSCs in Mouse Hypoderm

Example 10.2.1 is repeated for the hMSSCs differentiated in Examples 2.1.3-2.1.26 and Examples 2.2.3-2.2.26.

Example 11.1. Osteogenesis Test Using hMSC

For analysis of osteogenesis of hMSCs in a thighbone fracture model, hMSCs (Lonza, Switzerland) were cultured with a MSCGM-CD (Lonza, Switzerland) medium for 7 passages and then absorbed into a collagen membrane (SK Bioland, Korea) cut to a size of 1 mm×1 mm. After perforating one tibia of a 6-week-old Balb/c nude mouse about 1 mm using a drill (Bosch Professional, Germany), the hMSCs absorbed in the collagen membrane were inserted into the fracture site of the mouse. Every two weeks, the mouse was anesthetized and micro-CT (Skyscan 1076, Antwerp, Belgium) images were obtained for the fracture site. Immunohistochemistry and immunohistochemical staining were performed 6 weeks later.

Example 11.2.1. Osteogenesis Test Using hMSSC

For analysis of osteogenesis of hMSSCs in a thighbone fracture model, the hMSSCs of Example 2.1.2 were cultured with a MSCGM-CD (Lonza, Switzerland) medium for 2-5 passages and then absorbed into a collagen membrane (SK Bioland, Korea) cut to a size of 1 mm×1 mm. After perforating one tibia of a 6-week-old Balb/c nude mouse about 1 mm using a drill (Bosch Professional, Germany), the hMSSCs absorbed in the collagen membrane were inserted into the fracture site of the mouse. Every two weeks, the mouse was anesthetized and micro-CT (Skyscan 1076, Antwerp, Belgium) images were obtained for the fracture site. Immunohistochemistry and immunohistochemical staining were performed 6 weeks later.

Example 11.2.2. Osteogenesis Test Using hMSSCs

Example 11.2.1 is repeated for the hMSSCs differentiated in Examples 2.1.3-2.1.26 and Examples 2.2.3-2.2.26.

Example 12. Micro-CT

The bone formed in the kidney into which the hMSSCs were transplanted in Example 10.1 was scanned by micro-CT (Skyscan 1076, Antwerp, Belgium) to obtain 3D CT (computed tomography) images. Then, the data were digitalized with a frame grabber and the resulting images were transmitted to a computer using the Comprehensive TeX Archive Network (CTAN) topographic reconstruction software.

Example 13. Measurement of Scx, Runx2 and MYH9 mRNA Expression Levels

RNAs were extracted from the transplant of the hMSSCs of Example 2.1.2 in the kidney using 500 μL of Trizol (Life Technologies, USA) according to the manufacturer's protocol. After treating the transplant of the hMSSCs in the kidney with DNAse (RQ1 DNase, Promega, USA), 500 ng of RNAs were reversely transcribed to cDNAs using oligo-d(T) and random hexamers according to the Superscript III RT (Life Technologies, USA) first-strand cDNA synthesis protocol. qRT-PCR was conducted on the StepOne Plus PCR cycler (Applied Biosystems) using SYBR green (Applied Biosystems, Foster City, Calif.). mRNA expression data were analyzed using the ΔΔCT method and normalized with glyceraldehyde-3-phosphate dehydrogenase (GAPDH) for gene detection. The primers necessary for the qRT-PCR were purchased from Qiagen (USA). As a control group, RNAs were extracted from hMSSCs and qRT-PCR was conducted in the same manner.

Example 14. Differentiation of hMSSCs Derived from hESCs

Example 14.1. Aging Marker

The differentiation from hESCs to hMSSCs was induced as described in Example 2 and the morphological change of the induced hMSSCs was observed. The result is shown in FIG. 1A. As seen from FIG. 1A, it was confirmed that the undifferentiated single H9 hESCs were differentiated into cells with fibroblast morphology within 7 passages. They grew with similar morphologies for 10 passages or longer, from passage 7 to passage 17, and showed a positive response to staining with the aging marker β-galactosidase since passage 19, suggesting that aging was progressed.

Example 14.1. Pluripotency Marker by Immunofluorescence Method

Figure 1B:
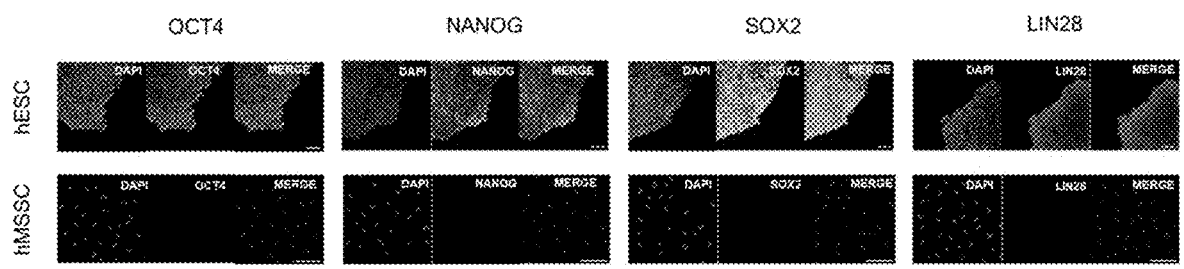

The expression of pluripotency markers (OCT4, NANOG, SOX2 and LIN28) in the hMSSCs after 7 passages or longer since the induction from the hESCs was observed by the immunofluorescence method. The result is shown in FIG. 1B. For comparison, the expression of pluripotency markers in H9 hESCs was investigated by the immunofluorescence method. As seen from FIG. 1B, the H9 hESCs were positive for all of OCT4, NANOG, SOX2 and LIN28, suggesting that they have pluripotency. In contrast, the hMSSCs induced from the H9 hESCs were negative for OCT4, NANOG, SOX2 and LIN28.

Figure 1C:
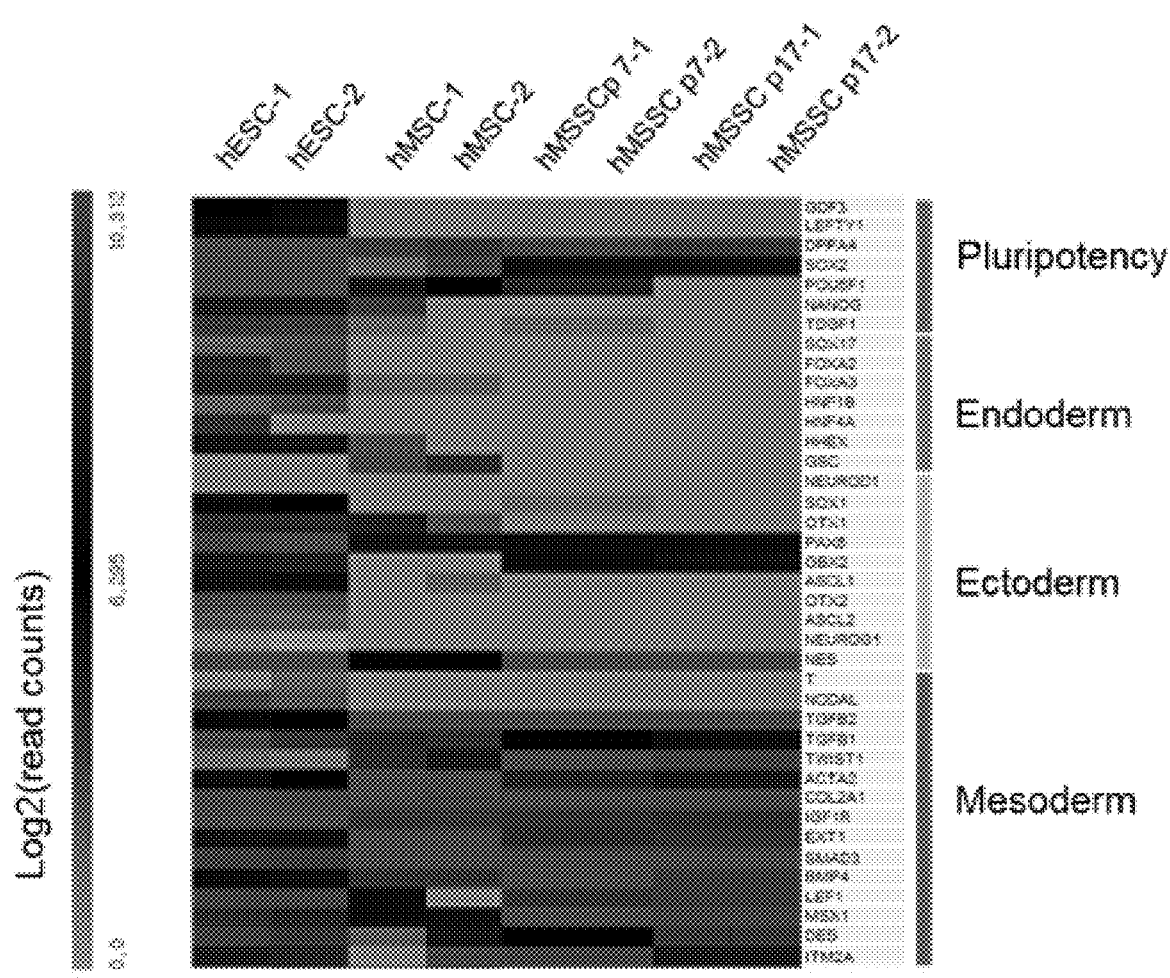
Figure 1D:
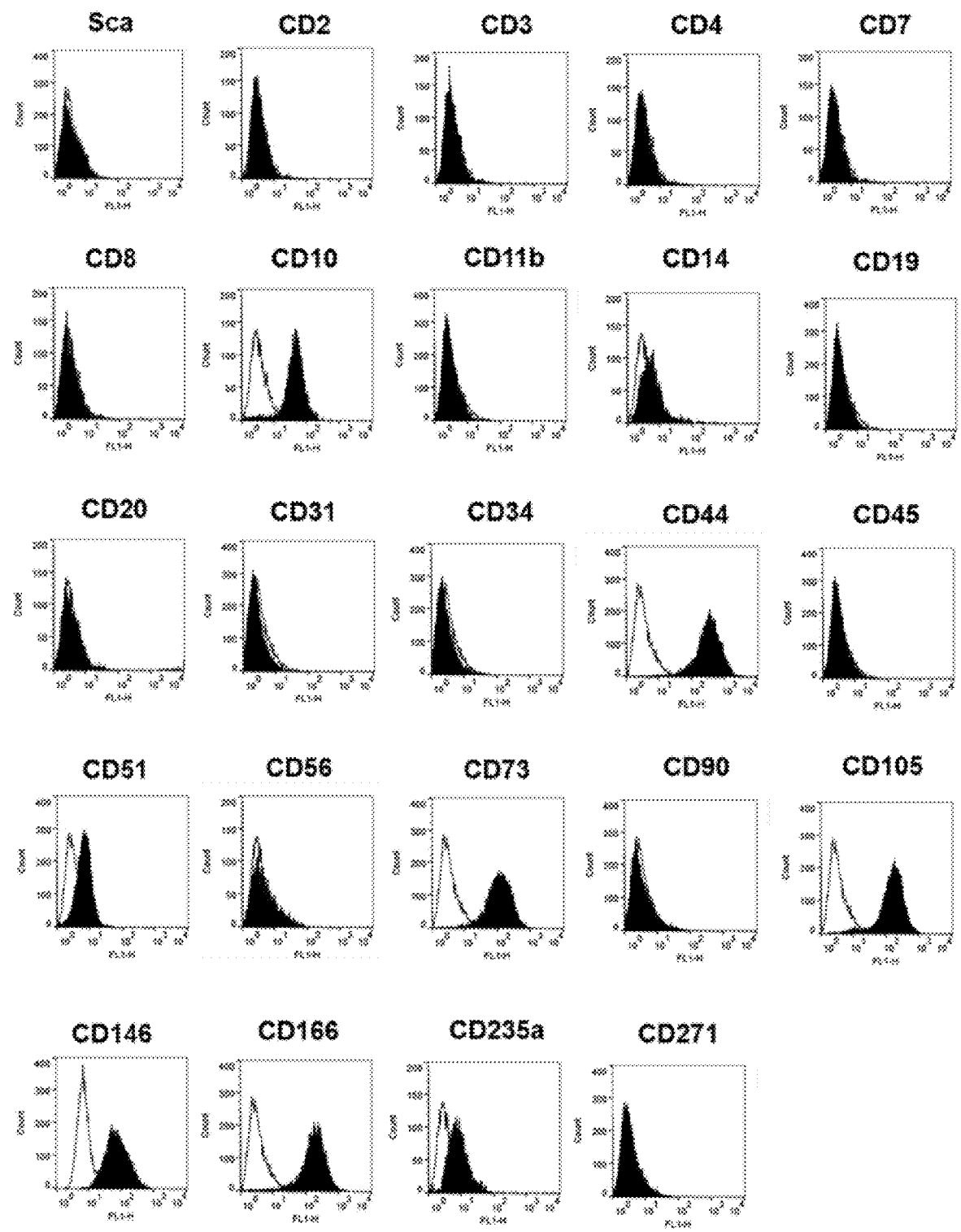

Example 14.2. Confirmation of Pluripotency, Ectodermal, Mesodermal and Endodermal Markers Through RNA Sequencing The expression of pluripotency, ectodermal, mesodermal and endodermal markers in hESCs, hMSCs and hMSSCs at passages 7 and 17 was investigated through RNA sequencing. The result is shown in FIG. 1C. The expression of the mRNAs of the pluripotency markers TDGF, NANOG, POU5F1, SOX2, DPPA4, LEFTY1, GDF3, etc. was confirmed in the H9 hESCs (hESC-1, hESC-2). In contrast, for the hMSSCs induced from the H9 hESCs, the expression of the pluripotency marker DPPA4 was observed but the expression of the pluripotency markers TDGF, NANOG, POU5F1, LEFTY1 and GDF3 was not observed. The expression level of DPPA4 was comparable to that in the H9 hESCs.

The expression of DPPA4 was not observed in the human mesenchymal stem cells. In addition, the hMSSCs were positive for the ectodermal marker NES, were positive for most mesodermal markers except for DES and the early mesodermal markers T and nodal and were negative for most endodermal markers. In particular, NES was not expressed in the mesenchymal stem cells.

Example 14.3. Confirmation of Mesenchymal Stem Cell Markers Through Expression of Cell Surface Antigens The expression of antigens on the surface of hMSSCs was measured as seen from FIG. 1D. When the expression of mesenchymal stem cell-specific cell surface antigens was investigated, the expression of the mesenchymal stem cell markers CD44, CD51, CD73, CD105, CD146 and CD166 was observed in the hMSSCs but the expression of the mesenchymal stem cell markers CD90 and CD271 was not observed. In addition, the expression of the vascular cell surface markers CD2, CD3, CD7, CD8, CD11b, CD14, CD19, CD20, CD31, CD34 and CD56 was not observed but the expression of the pre-B cell marker CD10 was observed.

Example 14.4. Confirmation of Other Cell-Specific Markers

Figure 1E:
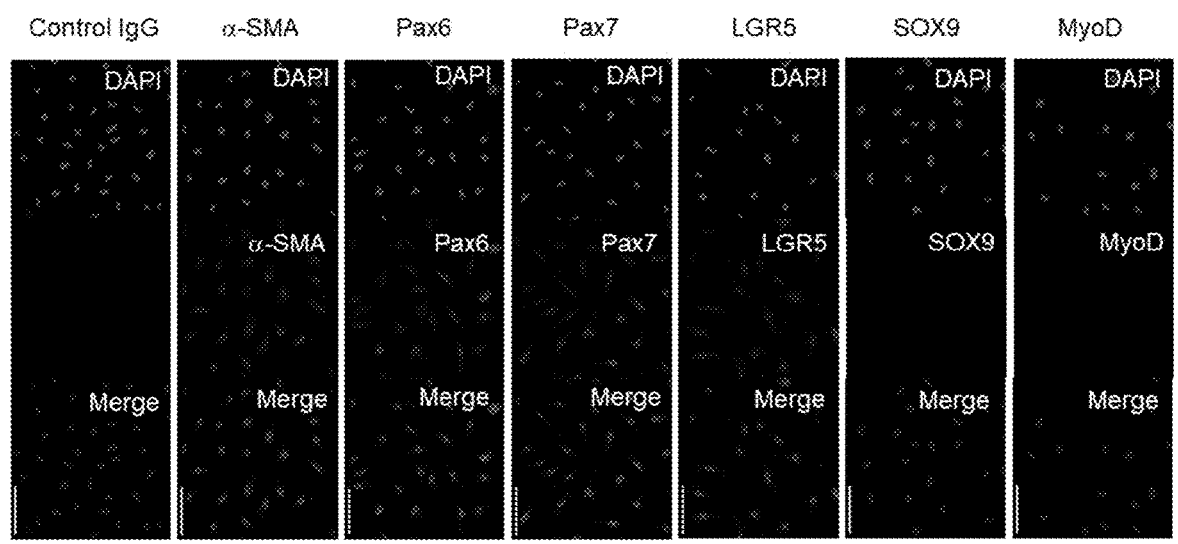

The expression of various tissue-specific markers was analyzed to investigate the characteristics of hMSSCs as shown in FIG. 1E. In the drawing, DAPI represents stained nuclei and the blue triangle indicates a β-galactosidase positive cell. The mesodermal marker alpha smooth muscle actin (a-SMA), the neuroectodermal marker Pax6, the myogenic satellite marker Pax7, and the intestinal stem cell marker LGR5 were expressed, whereas the chondrocyte marker SOX9 and the myoblast marker MyoD were not expressed. This suggests that the hMSSCs are progenitor cells prior to differentiation into cartilage cells and muscle cells.

Example 15.1. Differentiation Capacity of hMSSCs In Vitro

In-vitro osteogenesis, chondrogenesis and adipogenesis were tested in Example 7.1.1, Example 7.2.1 and Example 7.3.1 for hMSCs and the hMSSCs from Example 2.1.2 and the result is shown in FIG. 2A. From FIG. 2A, it was confirmed that the hMSCs could be differentiated into bone, cartilage and fat in vitro. Meanwhile, the hMSSCs were differentiated into bone and cartilage but were hardly differentiated into fat under the same conditions in vitro. That is to say, the cells were found to be functionally different from the mesenchymal stem cells.

Example 15.2. Differentiability into Skeletal Muscle

It was investigated whether the hMSSCs of Example 14 has the potential to be differentiate into skeletal muscle. The hMSSCs were cultured for 2 weeks in a medium for inducing differentiation into skeletal muscle (DMEM containing 2% B27) on a Matrigel-coated cover slip and then immunofluorescence assay was performed for the skeletal muscle marker MYH9. The result is shown in FIG. 2B. C2C12 cells were used as a control group. As seen from FIG. 2B, it was confirmed that the skeletal muscle-specific marker MYH9 was expressed when the hMSSCs were cultured in the skeletal muscle differentiation medium, suggesting that the hMSSCs have the potential to differentiate into skeletal muscle.

Example 15.3. Differentiability into Endothelial Cell

It was investigated whether the hMSSCs of Example 14 has the potential to differentiate into endothelial cells. The hMSSCs were cultured for 6 days in a medium for inducing differentiation into an EC (endothelial growth medium (EGM)-2 (Lonza, Walkersville, Md.)) supplemented with 50 ng/mL VEGF (vascular endothelial growth factor: ProSpec, Rehovot, Israel) and 10 ng/mL bFGF (basic fibroblast growth factor; ProSpec) and then immunofluorescence assay was performed for the endothelial cell markers CD31 and VE-cadherin. The result is shown in FIGS. 2C and 2D. HUVECs were used as a positive control group for endothelial cell differentiation. As seen from FIG. 2C and FIG. 2D, the expression of CD31 and VE-cadherin was not observed in the hMSSCs, suggesting that the hMSSCs lack the potential to differentiate into endothelial cells. In contrast, expression of the markers were observed in the control group HUVECs.

Example 15.4. Differentiability into Nerve Cell

The hMSSCs were incubated for 7 days in a medium for inducing differentiation into a nerve (Neurobasal medium containing 2% B27, 2 mM GlutaMAX and antibiotics) and then cultured for 3 days while adding 0.5 mM dibutyl cAMP (Sigma) every day. Then, immunofluorescence assay was performed for the nerve cell differentiation marker MAP2. The result is shown in FIG. 2E. NSCs (neuronal stem cells) were used as a positive control group for nerve cell differentiation. As seen from FIG. 2E, the cell morphology of the NSCs was changed to that of nerve cells and the expression of the nerve cell-specific marker MAP2 was observed, suggesting that the cells were differentiated into nerve cells. In contrast, the hMSSCs showed no change in cell morphology and the expression of MAP2 was not observed, suggesting that they lack the potential to be differentiate into nerve cells.

Although the hMSSCs were positive for the ectodermal marker NES as confirmed in Example 14, they were not differentiated into nerve cells. It was confirmed that the hMSSCs can be differentiated into the mesoderm, more particularly to bone, cartilage and muscle.

Example 16. Confirmation of Differentiation of hMSSCs into Bone, Cartilage, Muscle, Fat and Tendon In Vivo In order to measure the differentiability of the hMSSCs induced in the same manner as in Example 2 in vivo, the hMSSCs were transplanted into the kidney (Example 10.1) and hypoderm (Example 10.2) of an immune-deficient mouse. After transplanting the hMSSCs into mouse kidney and staining tissues with H&E 3-4 weeks later, immunofluorescence staining was performed for bone-, muscle-, fat- and tendon-specific markers and the cell nuclei were counterstained with TO-PRO3. The result is shown in FIG. 3A and FIG. 3B.

FIG. 3A shows images obtained 4 weeks after culturing the hMSSCs in a MSCGM-CD (Lonza, Switzerland) medium for 2-5 passages and transplanting them into the kidney. The H&E staining result shows that muscle, fat and tendon were formed well in the kidney. See (a) of FIG. 3A. When the differentiated muscle tissues were analyzed, the differentiation into skeletal muscle was observed but the differentiation into smooth muscle was not observed. In contrast, when human MSCs were transplanted under the same condition, muscle, fat, tendon, etc. were not formed at all (data not shown). When immunohistochemical assay was performed, it was confirmed that each differentiated tissue was positive for the muscle marker phospho-myosin light chain (pMLC), the adipose marker PPARgamma (PPAr), the tendon marker sleraxis (Scx), etc. and was also positive for the human cell marker hLA (human leukocyte antigen). From this, it can be seen that transplanted hMSSCs were differentiated into muscle, fat and tendon cells (This is contrary to the in-vitro test result showing no differentiation into fat). See (b) of FIG. 3A.

In FIG. 3B, (a) shows a result of micro-CT scanning showing that hard tissue, or bone, was formed at the site where the hMSSCs were transplanted into the kidney.

In FIG. 3B, (b) and (c) show a result of confirming bone formation by H&E and pentachrome staining. It can be seen that the transplanted hMSSCs were differentiated into bone in the kidney capsule.

In FIG. 3B, (d) shows the immunohistochemical assay at the transplanted site. It was confirmed that the cells in the tissue were positive for the human cell marker hLA (human leukocyte antigen), the bone markers Osx (osterix), Runx2, DMP1, OCN (osteocalin), etc. and the vascular marker vWF, suggesting that bone was confirmed. Therefore, it can be seen that the transplanted hMSSCs were differentiated into bone.

FIG. 3B, (a) 3C shows that the hMSSCs transplanted into mouse hypoderm by loading in fibrin glue to which hyaluronic acid was added were differentiated into cartilage cells. The cartilage formation was confirmed by H&E and toluidine blue staining.

Taken together, it was confirmed that the hMSSCs of the present disclosure can be differentiated into cartilage, muscle, tendon and bone at the transplanted site and have superior differentiation capacity.

Example 17. Confirmation of Fracture Recovery Effect of hMSSCs

In order to confirm the fracture recovery of hMSSCs induced in the same manner as in Example 2, osteogenesis test was performed as in Example 11. The result is shown in FIGS. 4A and 4B.

Figure 4A:
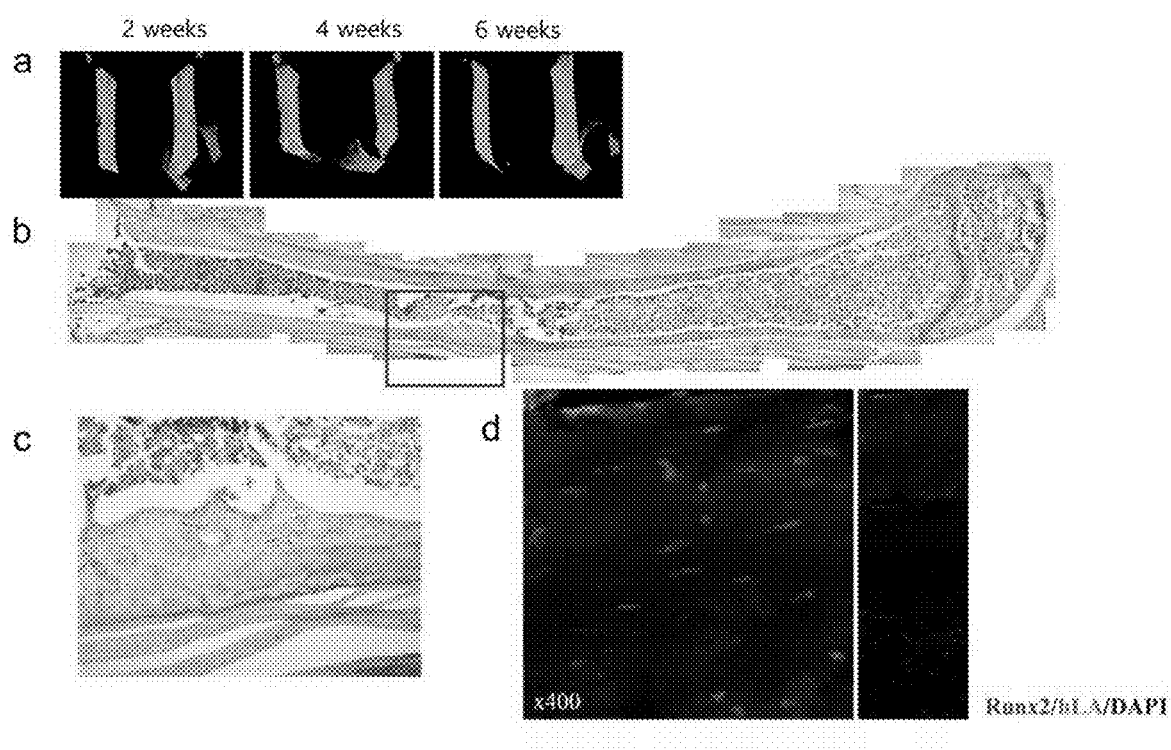
FIGS. 4A and 4B show the effect of hMSSCs on recovery of fracture according to Example 17.
Figure 4B:
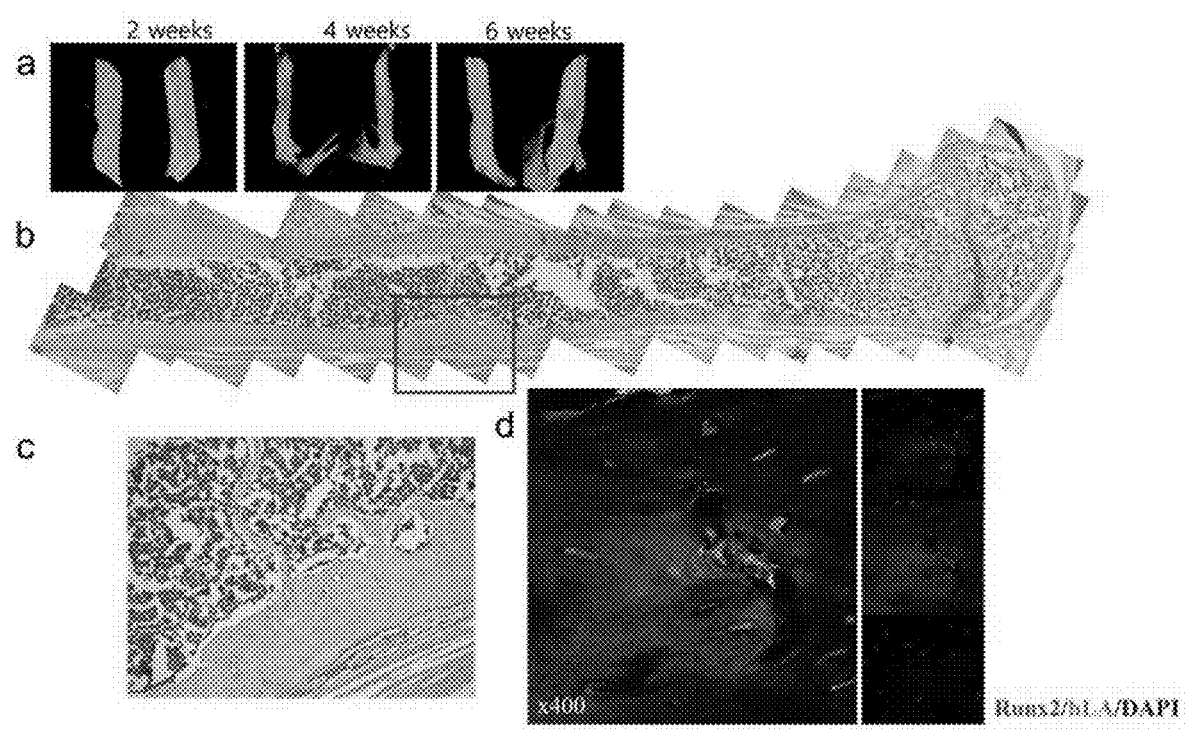

FIG. 4A shows that, when the hMSCs were transplanted into a fracture site in a thighbone fracture model, bone was formed about 6 weeks later at the fracture site. However, because the osteogenic site was positive for the bone marker Runx2 but negative for the human cell marker hLA, it was estimated that the osteogenesis was not by the transplanted hMSCs but by the mouse cells. In FIG. 4A, (a) shows micro-CT images obtained 2, 4 and 6 weeks after the transplantation of hMSCs into the fracture site; (b) shows a result of H&E immunohistochemistry of the thighbone containing the fracture site into which hMSCs were transplanted; (c) shows a result of magnifying the red square portion of (b); and (d) shows a result of confirming that the transplanted hMSCs were not differentiated into bone cells by immunohistochemistry for the bone cell marker Runx2 and the human cell marker hLA.

In contrast, when hMSSCs were transplanted under the same condition, bone was formed about 6 weeks later at the fracture site, with the osteogenic site being positive for Runx2 and positive for the human cell marker hLA. In FIG. 4B, (a) shows micro-CT images obtained 2, 4 and 6 weeks after the transplantation of hMSSCs into the fracture site; (b) shows a result of H&E immunohistochemistry of the thighbone containing the fracture site into which hMSSCs were transplanted; (c) shows a result of magnifying the red square portion of (b); and (d) shows a result of confirming that the transplanted hMSSCs were differentiated into bone cells by immunohistochemistry for the bone cell marker Runx2 and the human cell marker hLA. This suggests that the bone formation was owing to the differentiation of the hMSSCs.

Figure 5A:
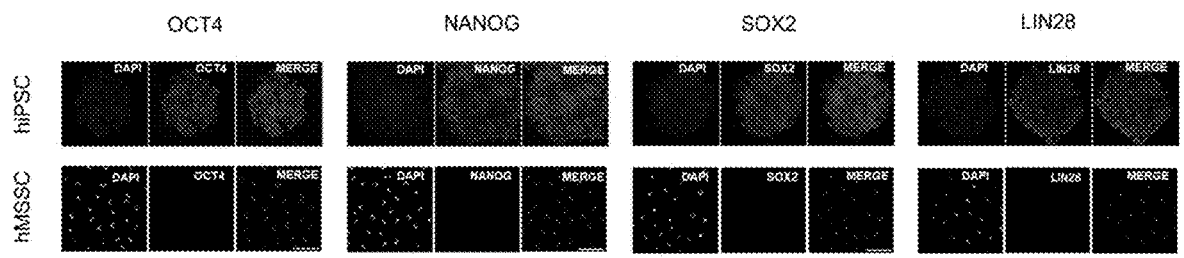
FIGS. 5A-5D show differentiation of hiPSCs into hMSSCs like hESCs according to Example 18.

Example 18. Induction of Differentiation from hiPSCs into hMSSCs and Characterization of Induced hiPSCs hiPSCs (human induced pluripotent stem cells) were prepared by reprogramming embryonic BJ fibroblast (ATCC®CRL2522™) by overexpressing OCT4, KLF4, SOX2 and MYC using Sendai virus according to the method developed by Hasegawa et al. (Fusaki et al., 2009).

iPS-hMSSCs were obtained by inducing hMSSCs from hiPSCs in the same manner as in Example 2. The expression level of the pluripotency markers Oct4, Nanog, Sox2 and Lin28 in the iPS-hMSSCs was investigated by immunofluorescence assay and RT-PCR. The result is shown in FIG. 5A. As seen from FIG. 5A, iPS cells were positive for OCT4, NANOG, SOX2 and LIN28, suggesting that the cells have pluripotency. In contrast, the iPS-hMSSCs were negative for the pluripotency markers OCT4, NANOG, SOX2 and LIN28.

Figure 5B:
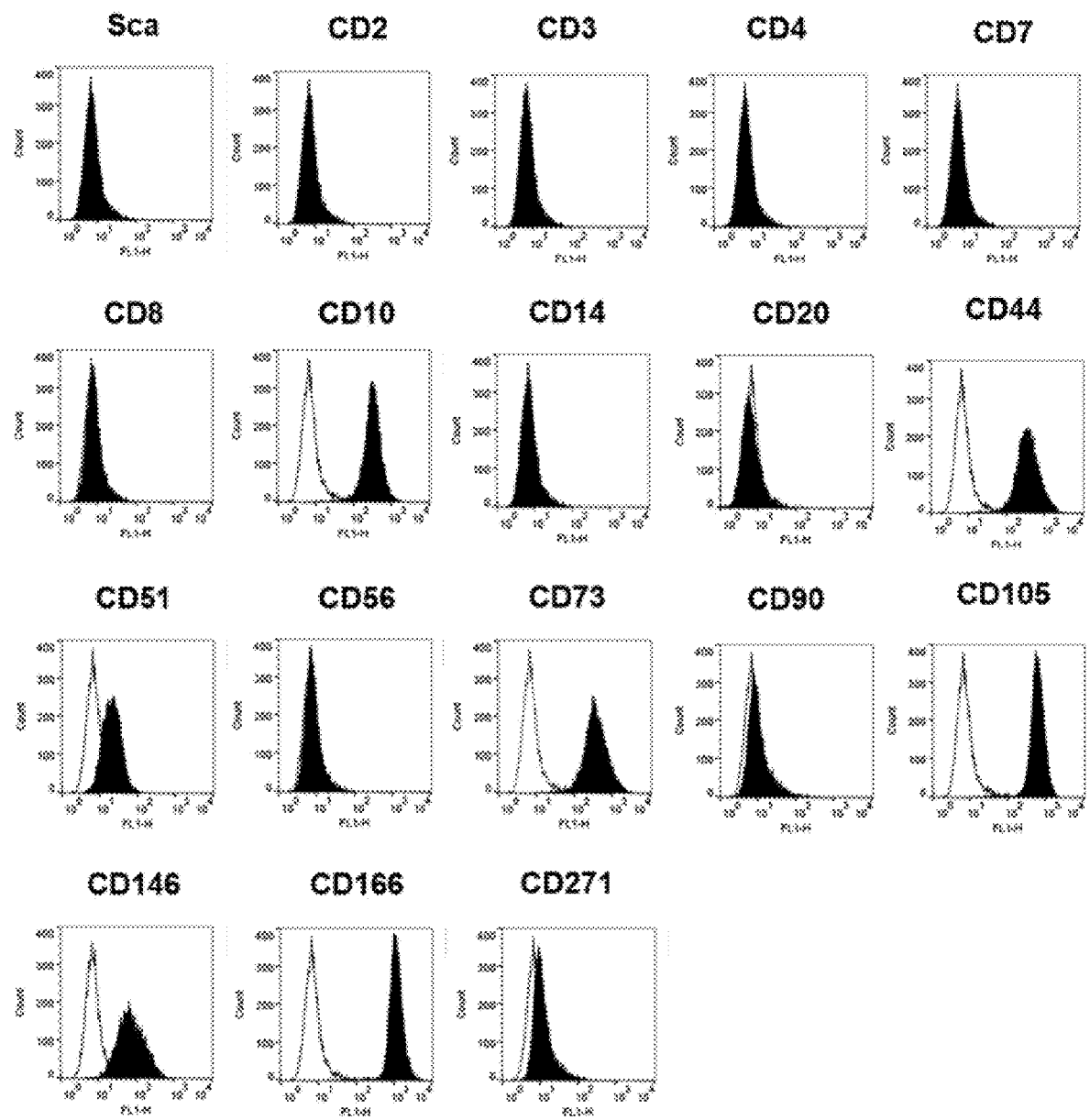

FIG. 5B shows a result of measuring the expression of surface antigens for the iPS-hMSSCs. When the expression of mesenchymal stem cell-specific cell surface antigens was investigated, it was confirmed that, among the mesenchymal stem cell markers, CD44, CD51, CD73, CD105, CD146 and CD166 were expressed in the iPS-hMSSCs, but CD90 and CD271 were not expressed in the iPS-hMSSCs. In addition, the pre-B cell marker CD10 was expressed whereas the vascular cell surface markers CD2, CD3, CD7, CD8, CD14, CD20 and CD56 were not expressed.

Figure 5C:
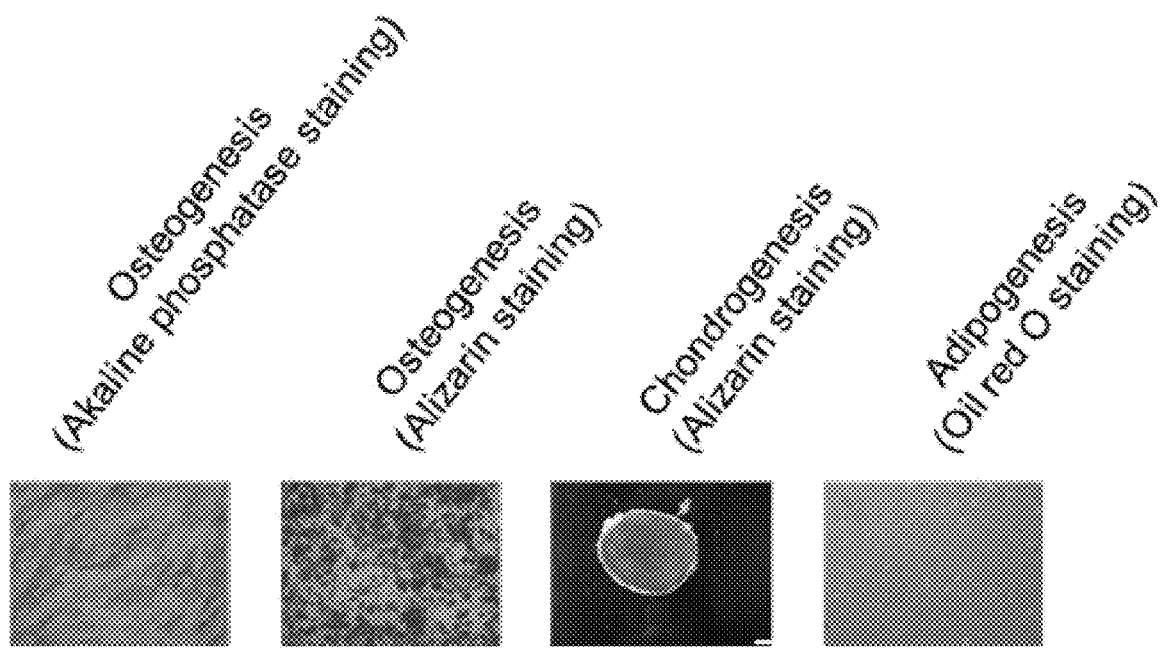

Also, the osteogenesis, chondrogenesis and adipogenesis of the iPS-hMSSCs were evaluated in the same manner as in Example 15.1. The result is shown in FIG. 5C. As seen from FIG. 5C, it was confirmed that the hMSSCs induced from the hiPSCs were differentiated into bone and cartilage in vitro but were hardly differentiated into fat.

Figure 5D:
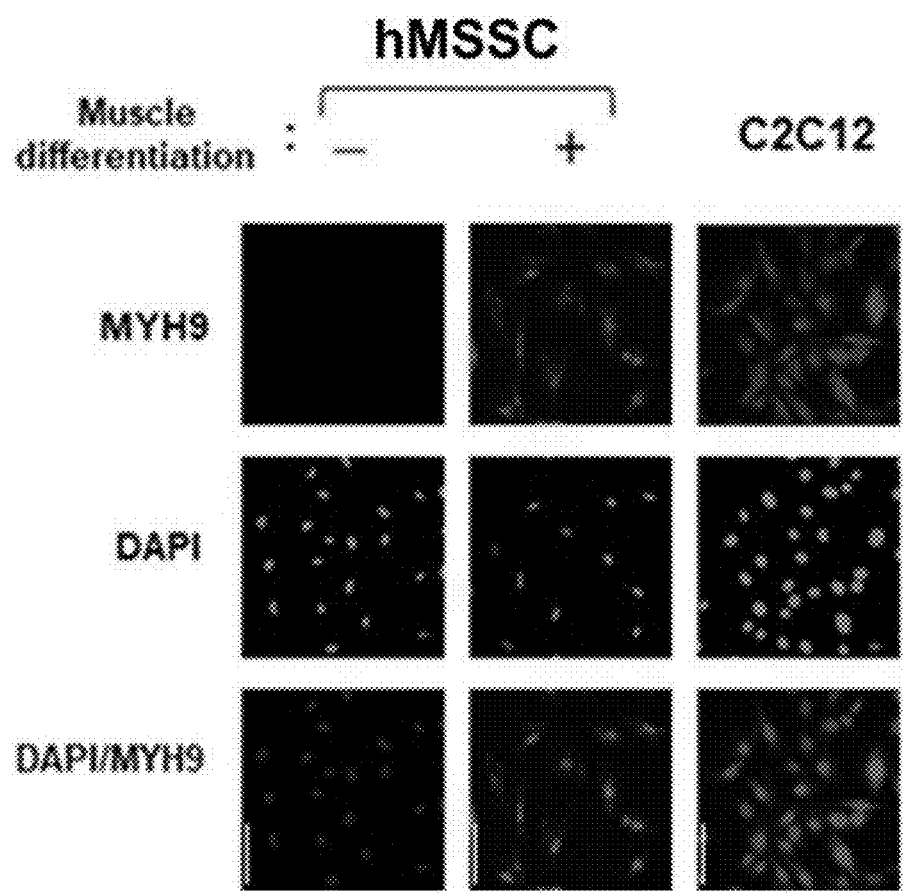

In addition, the iPS-hMSSCs were cultured for 2 weeks in a medium for inducing differentiation into skeletal muscle (DMEM containing 2% B27) on a Matrigel-coated cover slip and then immunofluorescence assay was performed for the skeletal muscle marker MYH9. The result is shown in FIG. 5D. C2C12 cells were used as a control group. As seen from FIG. 5D, it was confirmed that the hMSSCs induced from the hiPSCs have the potential to differentiate into skeletal muscle.

Taken together, it was confirmed that the hMSSCs induced from the hiPSCs have the same characteristics as the hMSSCs induced from the hECSs, suggesting that hMSSCs can be obtained using hiPSCs instead of hECSs.

Example 19. Differentiability of hMSSCs Induced from hiPSCs In Vivo

Example 19.1. Transplantation into Kidney

After transplanting the hMSSCs of Example 18 into mouse kidney, the tissue was stained with H&E 3-4 weeks later. It was confirmed that muscle, fat and tendon were formed in the kidney. The immunohistochemical assay result for the transplanted site was positive for the muscle marker phospho-myosin light chain (pMLC), the adipose marker PPARgamma (PPAr), the tendon marker sleraxis (Scx), etc. and also positive for the human cell marker hLA (human leukocyte antigen). Also, the result was positive for the bone markers Osx (osterix), Runx2, DMP1, OCN (osteocalin), etc. Through this, it was confirmed that the hMSSCs induced from the iPSCs can be differentiated into muscle, fat, tendon and bone.

Example 19.2. Transplantation into Hypoderm

When the hMSSCs of Example 18 were transplanted into mouse hypoderm by loading in fibrin glue to which hyaluronic acid was added, it was confirmed through H&E and toluidine blue staining that the hMSSCs can be differentiated into cartilage.

Example 20. Comparison of Differentiation Capacity of Noggin-Containing MSSC Medium and Conditioned Medium-Containing CM Medium The differentiation capacity of a medium (hereinafter, "CM medium") obtained by replacing the human noggin (Life Technologies), i.e., the constitutional ingredient 1) of the seven constitutional ingredients of the MSSC medium of Example 2, with a conditioned medium (a culture supernatant obtained after culturing CF1 cells with a medium obtained by replacing DMEM/F12 in a complete medium with knockout DMEM (supplemented with 20% knockout serum replacement (Invitrogen, USA), 1 mM glutamine, 1% nonessential amino acids (Invitrogen, USA), 0.1 mM β-mercaptoethanol, 0.1% penicillin-streptomycin and 5 mg/mL bovine serum albumin)) (the remaining constitutional ingredients 2)-7) are identical) was compared with that of the MSSC medium.

Noggin is generally used to maintain the characteristics of hESCs during culturing (Chaturvedi G, Simone P D, Ain R, Soares M J, Wolfe M W. Noggin maintains pluripotency of human embryonic stem cells grown on Matrigel. *Cell Prolif.* 2009 August; 42(4): 425-33). Contrarily to the previously known mechanism, it significantly increased the tendency toward the mesoderm. As can be seen from Table 1, the tendency for osteogenic differentiation was increased 10 times or greater when noggin was contained, as compared when the CM medium was used.

TABLE 1

Differentiation tendency of MSSC medium vs. CM medium (number of observations out of 20 differentiations)

| Medium | Bone | Muscle | Tendon | Fat |
|---|---|---|---|---|
| CM medium | 1/20 | 20/20 | 2/20 | 2/20 |
| Noggin-containing medium | 15/20 | 20/20 | 10/20 | 12/20 |

Figure 6:
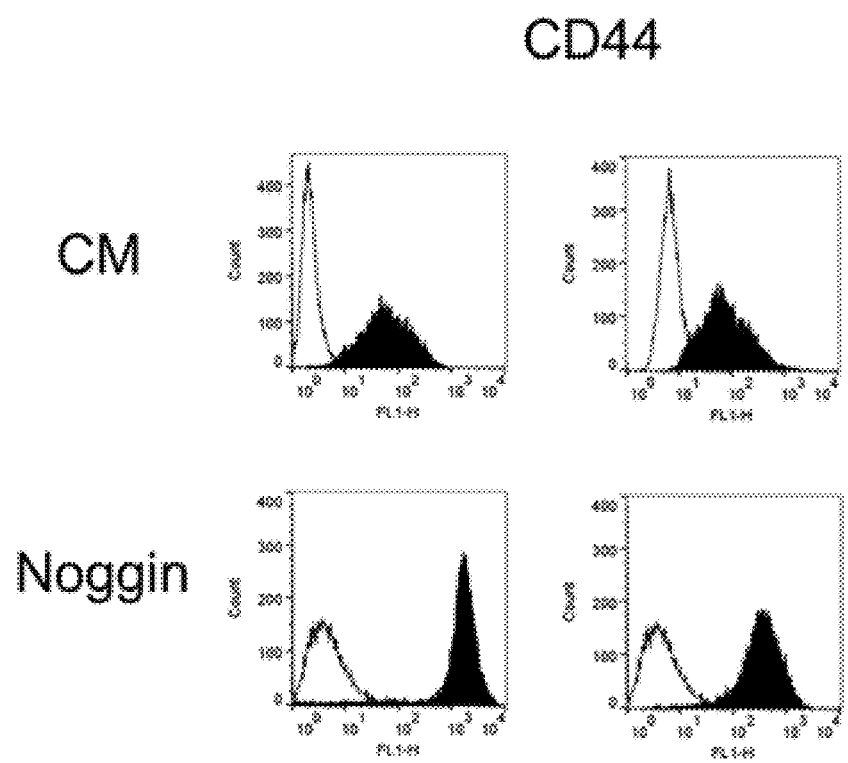
FIG. 6 shows expression level of CD44 in a CM medium and in hMSSCs according to Example 20.

Also, the expression level of CD44 was compared for the two media. After inducing differentiation using the CM-containing medium (CM medium) and the noggin-containing medium (MSSC medium), the expression level of CD44 was measured in the same manner as in Example 6. As a result, it was confirmed that the expression level of CD44 was increased remarkably when the noggin-containing MSSC medium was used as compared to when the CM medium was used. See FIG. 6.

During osteogenic differentiation, the formation of endochondral bone occurs only after chondrogenesis. CD44 is known to play an essential role in chondrogenesis (Wu S C, Chen C H, Chang J K, Fu Y C, Wang C K, Eswaramoorthy R, Lin Y S, Wang Y H, Lin S Y, Wang G J, Ho M L: Hyaluronan initiates chondrogenesis mainly via cd44 in human adipose-derived stem cells. J Appl Physiol (1985) 2013; 114: 1610-1618). From the above results, it can be seen that use of the MSSC medium rather than the CM medium is suitable for osteogenic differentiation.

When hMSSCs were transplanted into the kidney, the cells differentiated by the hMMSC medium showed 1-2 weeks faster differentiation as compared to the cells differentiated by the CM medium. The difference in differentiation speed when the CM medium was used and when the hMMSC medium was used is shown in Table 2.

TABLE 2

Differentiation speed of MSSC medium vs. CM medium (increased mRNA level as compared to before transplantation of hMSSCs)

| mRNA level | | Week 1 | Week 2 | Week 3 | Week 4 |
|---|---|---|---|---|---|
| MYH9 | CM | 1.3 ± 0.1 | 2.1 ± 0.1 | 5.1 ± 0.3 | 12.5 ± 3.1 |
| | MSSC | 2.2 ± 0.3 | 4.4 ± 0.4 | 20.1 ± 3.1 | 23.1 ± 3.4 |
| Runx2 | CM | 1.2 ± 0.3 | 1.8 ± 0.3 | 3.6 ± 0.3 | 6.5 ± 3.1 |
| | MSSC | 2.1 ± 0.2 | 4.3 ± 0.3 | 7.1 ± 0.3 | 13.3 ± 3.1 |
| Scx | CM | 1.3 ± 0.2 | 2.3 ± 1.2 | 5.2 ± 1.3 | 10.7 ± 2.2 |
| | MSSC | 2.1 ± 0.2 | 4.7 ± 1.5 | 12.1 ± 0.3 | 16.5 ± 2.9 |

Example 21. Comparison of Synergistic Effect for Combinations of Constitutional Ingredients of MSSC Medium The differentiation capacity of the MSSC medium of Example 2.1.2 not containing one of the constitutional ingredients 1)-6) was compared with that of the MSSC medium. As a result, it was confirmed that differentiation into cartilage (Alcian blue) or bone (ALP and Alizarin red S) was not achieved well when one of the constitutional ingredients 1)-6) was absent. See FIG. 7 and Table 3.

TABLE 3

Comparison of differentiation capacity of MSSC medium vs. medium deficient in one constitutional ingredient

| Constitutional ingredient of MSSC medium | 7 ingredients | TGF-β/activin/nodal signaling inhibitor (—) | hLIF (—) | ERK signaling inhibitor (—) | Wnt signaling activator (—) | Noggin (—) | FGF-2 signaling activator (—) |
|---|---|---|---|---|---|---|---|
| 1) Noggin | Yes | Yes | Yes | Yes | Yes | No | Yes |
| 2) LIF | Yes | Yes | No | Yes | Yes | Yes | Yes |
| 3) FGF-2 signaling activator | Yes | Yes | Yes | Yes | Yes | Yes | No |
| 4) Wnt signaling activator | Yes | Yes | Yes | Yes | No | Yes | Yes |
| 5) ERK signaling inhibitor | Yes | Yes | Yes | No | Yes | Yes | Yes |
| 6) TGF-β/activin/nodal signaling inhibitor | Yes | No | Yes | Yes | Yes | Yes | Yes |
| Remarks | Differentiated into muscle (including adipose), cartilage and bone | Not differentiated into muscle or cartilage | Not differentiated into cartilage | Differentiated into cartilage and bone was inhibited | Differentiated into bone was inhibited | MSSCs were not induced | MSSCs were not induced |

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method of preparing musculoskeletal stem cells (MSSCs), the method comprising:
    culturing cells comprising embryonic stem cells (ESCs) or induced pluripotent stem cells (iPSCs) in a culture medium composition,
    wherein the culture medium composition comprises noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor,
    wherein the cells, after the culturing, are MSSCs and exhibit the following characteristics:
    positive for nestin (NES);
    positive for Pax7;
    positive for α-SMA;
    negative for LIN28; and
    negative for CD90.
2. The method of claim 1, wherein the cells cultured in the culture medium composition comprise ESCs and do not comprises iPSCs.

3. The method of claim 1, wherein the cells cultured in the culture medium composition comprise iPSCs and do not comprises ESCs.

4. The method of claim 1, wherein the cells cultured in the culture medium composition comprise both iPSCs and ESCs.

5. The method of claim 1, wherein the Wnt signaling activator comprises at least one selected from the group consisting of SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), kenpaullone (9-bromo-7,12-dihydro-indolo[3,2-d]-[1]benzazepin-6(5H)-one), CHIR99021 (9-bromo-7,12-dihydro-pyrido[3',2':2,3]azepino[4,5-b]indol-6(5H)-one), CP21R7 (3-(3-amino-phenyl)-4-(1-methyl-1H-indol-3-yl)-pyrrole-2,5-dione), SB203580 (4-(4-fluorophenyl)-2-(4-methylsulfinylphenyl)-5-(4-pyridyl)-1H-imidazole), H-89 (5-isoquinolinesulfonamide), purmorphamine (2-(1-naphthoxy)-6-(4-morpholinoanilino)-9-cyclohexylpurine) and IQ-1 (2-(4-acetyl-phenylazo)-2-[3,3-dimethyl-3,4-dihydro-2H-isoquinolin-(1E)-ylidene]-acetamide).

6. The method of claim 1, wherein the ERK signaling inhibitor comprises at least one selected from the group consisting of AS703026 (N-[(2S)-2,3-dihydroxypropyl]-3-[(2-fluoro-4-iodophenyl)amino]-isonicotinamide), AZD6244 (6-(4-bromo-2-chloroanilino)-7-fluoro-N-(2-hydroxyethoxy)-3-methylbenzimidazole-5-carboxamide), PD0325901 (N-[(2R)-2,3-dihydroxypropoxy]-3,4-difluoro-2-[(2-fluoro-4-iodophenyl)amino]-benzamide), ARRY-438162 (5-[(4-bromo-2-fluorophenyl)amino]-4-fluoro-N-(2-hydroxyethoxy)-1-methyl-1H-benzimidazole-6-carboxamide), RDEA119 ((S)—N-(3,4-difluoro-2-((2-fluoro-4-iodophenyl)amino)-6-methoxyphenyl)-1-(2,3-dihydroxypropyl)cyclopropane-1-sulfonamide), GDC0973 ([3,4-difluoro-2-(2-fluoro-4-iodoanilino)phenyl]-3-hydroxy-3-[(2S)-piperidin-2-yl]-azetidin-1-yl-methanone), TAK-733 ((R)-3-(2,3-dihydroxypropyl)-6-fluoro-5-(2-fluoro-4-iodophenylamino)-8-methylpyrido[2,3-d]pyrimidine-4,7(3H,8H)-dione), RO5126766 (3-[[3-fluoro-2-(methylsulfamoylamino)-4-pyridyl]methyl]-4-methyl-7-pyrimidin-2-yloxychromen-2-one) and XL-518 ([3,4-difluoro-2-[(2-fluoro-4-iodophenyl)amino]phenyl][3-hydroxy-3-[(2S)-2-piperidinyl]-1-azetidinyl]methanone).

7. The method of claim 1, wherein the TGF-3/activin/nodal signaling inhibitor comprises at least one selected from the group consisting of E-616452 (2-[3-(6-methyl-2-pyridinyl)-1H-pyrazol-4-yl]-1,5-naphthyridine), A-83-01 (3-(6-methyl-2-pyridinyl)-N-phenyl-4-(4-quinolinyl)-1H-pyrazole-1-carbothioamide) and SB431542 (4-[4-(1,3-benzodioxol-5-yl)-5-(2-pyridinyl)-1H-imidazol-2-yl]benzamide).

8. The method of claim 1, wherein the culturing is performed for at least 5 passages without changing the ingredients of the culture medium composition.

9. The method of claim 1, wherein the culturing is performed for 5 to 25 passages without changing the ingredients of the culture medium composition.

10. The method of claim 8, wherein the culturing is performed while maintaining the concentrations of the ingredients in the culture medium composition.

11. The method of claim 1, wherein the cells, after the culturing, further have a characteristic of positive for CD146.

12. The method of claim 1, wherein the cells, after the culturing, further have at least one of the following characteristics:

negative for OCT4;
negative for NANOG;
negative for SOX2; and
negative for LIN28.

13. The method of claim 12, wherein the cells, after the culturing, further have a characteristic of negative for CD271.

14. The method of claim 12, wherein the cells, after the culturing, are configured to differentiate into mesoderm but not into ectoderm or endoderm.

15. The method of claim 12, wherein the cells, after the culturing, are configured to differentiate into muscle, bone, cartilage, tendon, or ligament.

16. The method of claim 12, wherein the cells, after the culturing, are configured to differentiate into a nerve cell.

17. The method of claim 12, wherein the cells, after the culturing, are configured to differentiate into an endothelial cell.

18. The method of claim 12, wherein the cells, after the culturing, comprise a cell deposited under the accession number KCLRF-BP-00460.

19. A method of in vitro differentiation of MSSCs, the method comprising,
performing the method of claim 1, wherein the culture medium is referred to as a first culture medium;
collecting MSSCs from the cell composition;
in vitro culturing the collected MSSCs in a second culture medium; and
collecting cells differentiated from at least part of the MSSCs.

20. A method of preparing musculoskeletal cells, the method comprising:
performing the method of claim 1, wherein the culture medium is referred to as a first culture medium;
collecting MSSCs from the cell composition;
in vitro culturing the collected MSSCs in a second culture medium; and
transplanting at least part of the MSSCs into a mass of tissues such that the at least part of the MSSCs differentiates into musculoskeletal cells in the mass of tissues.

21. A method of treating a musculoskeletal disease, the method comprising:
performing the method of claim 1, wherein the culture medium is referred to as a first culture medium;
collecting MSSCs from the cell composition; and
administering, to a subject in need to such treatment, an effective amount of the collected MSSCs.

22. The method of claim 2, wherein the cells, after the culturing, further have the following characteristics:
negative for OCT4;
negative for NANOG;
negative for SOX2; and
negative for LIN28.

23. The method of claim 1, wherein the cells, after the culturing, further have at least one of the following characteristics:
negative for TDGF;
negative for NANOG;
negative for POU5F1;
negative for LEFTY1; and
negative for GDF3.

24. The method of claim 1, wherein the cells, after the culturing, further have at least one of the following characteristics:
positive for CD44;
positive for CD51;

positive for CD73;
positive for CD105;
positive for CD146;
positive for CD166;
negative for CD90; and
negative for CD271.

25. The method of claim 1, wherein the cells, after the culturing, further have the following characteristics:
positive for CD10;
negative for CD2;
negative for CD3;
negative for CD7;
negative for CD8;
negative for CD14;
negative for CD20; and
negative for CD56.

26. The method of claim 1, wherein the culturing is performed for at least 7 passages without changing the ingredients of the culture medium composition.

27. The method of claim 1, wherein the culturing is performed for at least 10 passages without changing the ingredients of the culture medium composition.

28. The method of claim 1, wherein the culturing is performed for 7 passages to 17 passages without changing the ingredients of the culture medium composition.

* * * * *